US009928339B2

(12) United States Patent
Tolle et al.

(10) Patent No.: US 9,928,339 B2
(45) Date of Patent: Mar. 27, 2018

(54) METHODS AND SYSTEMS FOR ROUTING IMAGE REPORTS

(71) Applicant: Merge Healthcare Incorporated, Chicago, IL (US)

(72) Inventors: Steven Tolle, Chicago, IL (US); Kochuparambil Harish, Chicago, IL (US); Atul Agarwal, Mississauga (CA); Pete Nanos, Chicago, IL (US)

(73) Assignee: Merge Healthcare Incorporated, Chicago, IL (US)

( * ) Notice: Subject to any disclaimer, the term of this patent is extended or adjusted under 35 U.S.C. 154(b) by 372 days.

(21) Appl. No.: 14/676,234

(22) Filed: Apr. 1, 2015

(65) Prior Publication Data

US 2015/0278385 A1 Oct. 1, 2015

Related U.S. Application Data

(60) Provisional application No. 61/973,728, filed on Apr. 1, 2014.

(51) Int. Cl.
G06F 17/30 (2006.01)
G06F 19/00 (2018.01)

(52) U.S. Cl.
CPC ........ *G06F 19/321* (2013.01); *G06F 17/3028* (2013.01); *G06F 19/328* (2013.01); *G06F 19/345* (2013.01); *G06F 19/3487* (2013.01)

(58) Field of Classification Search
None
See application file for complete search history.

(56) References Cited

U.S. PATENT DOCUMENTS

| 5,666,490 | A | 9/1997 | Gillings et al. |
| 6,260,021 | B1 * | 7/2001 | Wong .................... G06F 19/321 705/1.1 |
| 6,473,796 | B2 | 10/2002 | Tanaka |
| 6,819,785 | B1 * | 11/2004 | Vining .............. G06F 17/30056 128/922 |

(Continued)

OTHER PUBLICATIONS

International Search Report and Written Opinion for Application No. PCT/US15/23844 dated Sep. 1, 2015 (25 pages).

(Continued)

*Primary Examiner* — Richard Bowen
(74) *Attorney, Agent, or Firm* — Michael Best & Friedrich LLP

(57) ABSTRACT

Methods and systems for routing image reports. One method includes receiving a completed report for the image study from a report source, establishing a unique identifier for a set of images associated with the completed report and stored in an image repository accessible through an image viewer, storing the unique identifier and an identifier of the image viewer in an image directory, and automatically creating a link associated with the completed report, the link based on the unique identifier. The method also includes identifying a report destination for the completed report, and transmitting the completed report and the link to the report destination. In addition, the method includes, when a recipient selects the link, automatically identifying the image viewer based on the image directory, and automatically providing the recipient with access to the image viewer.

20 Claims, 30 Drawing Sheets

(56) References Cited

U.S. PATENT DOCUMENTS

| | | |
|---|---|---|
| 7,068,309 B2 | 6/2006 | Toyama et al. |
| 7,209,578 B2 | 4/2007 | Saito et al. |
| 7,333,227 B2 | 2/2008 | Seto |
| 7,386,462 B2 * | 6/2008 | Silva-Craig ............ G06F 19/321 382/128 |
| 7,423,771 B2 | 9/2008 | Ohata et al. |
| 7,885,822 B2 | 2/2011 | Akers et al. |
| 8,046,240 B2 | 10/2011 | Fukatsu et al. |
| 8,131,562 B2 | 3/2012 | Hernandez et al. |
| 8,233,750 B2 | 7/2012 | Minakuchi et al. |
| 8,527,635 B2 | 9/2013 | Jeon et al. |
| 8,566,367 B2 | 10/2013 | Matsue et al. |
| 8,577,696 B2 | 11/2013 | Fram et al. |
| 9,710,599 B1 | 7/2017 | Johnson et al. |
| 2002/0016821 A1 | 2/2002 | Son et al. |
| 2002/0046346 A1 | 4/2002 | Evans |
| 2002/0087359 A1 | 7/2002 | Bocionek |
| 2004/0204837 A1 | 10/2004 | Singleton |
| 2006/0010013 A1 | 1/2006 | Yamatake |
| 2006/0271403 A1 | 11/2006 | Iwasa et al. |
| 2007/0094052 A1 | 4/2007 | Blas |
| 2007/0100660 A1 | 5/2007 | Carosso et al. |
| 2008/0086335 A1 | 4/2008 | Matsue et al. |
| 2008/0144897 A1 | 6/2008 | Lal et al. |
| 2008/0208912 A1 | 8/2008 | Garibaldi |
| 2008/0247676 A1 | 10/2008 | Minakuchi et al. |
| 2009/0204435 A1 | 8/2009 | Gale |
| 2010/0228721 A1 * | 9/2010 | Mok ..................... G06F 19/322 707/711 |
| 2011/0110568 A1 | 5/2011 | Vesper et al. |
| 2011/0119088 A1 * | 5/2011 | Gunn .................... G06F 19/322 705/3 |
| 2011/0166875 A1 | 7/2011 | Hayter et al. |
| 2011/0282688 A1 | 11/2011 | Raggousis |
| 2012/0020536 A1 | 1/2012 | Moehrle |
| 2012/0065995 A1 | 3/2012 | Singh et al. |
| 2012/0116816 A1 | 5/2012 | Smith |
| 2012/0158717 A1 | 6/2012 | Unay et al. |
| 2012/0215799 A1 * | 8/2012 | Bohner ................. G06F 19/322 707/755 |
| 2012/0246741 A1 | 9/2012 | Klotz et al. |
| 2013/0110537 A1 | 5/2013 | Smith |
| 2013/0218597 A1 | 8/2013 | Lorsch et al. |
| 2015/0012300 A1 | 1/2015 | Smith |
| 2015/0363555 A1 | 12/2015 | Studsrud |
| 2017/0039529 A1 * | 2/2017 | Reicher ............... G06F 19/3487 |

OTHER PUBLICATIONS

Office Action from the United States Patent and Trademark Office for U.S. Appl. No. 14/676,248 dated Oct. 3, 2017 (33 pages).

* cited by examiner

Beachside Imageing Center
100 Mulligan Drive
Suite 100
Datona Beach, FL 52117
395-555-1221

PATIENT NAME: Test, Sarah
DATE OF BIRTH: 07/23/1978
JACKET # 1890
REFERRING DOCTOR:     GREENE, MARK
73222ARTH            MR Shoulder Arthogram
REASON      Annual Exam
TECHNIQUE: Magnetic Resonance imaging of the shoulder was preformed following intramuscular injection of Cadolinium under Endoscopic technique

FINDINGS:
There is linear hypeincanse signal undercutting the superior labrum parafecting the caseecus cortex of the glenoid tissue favoring the dignosis of normal unsettling of hydaliine cartilage rather then a lateral tear. A small superior lateral tear howeverm cannot be completly excluded.

There is a lateral tear of the posterior glenoid latrum expanding into the postextenior glcroid tissue. The tear extends into the posterior band of the interior glenatteral ligament (PAIGHL). There is no demonstrated reverse Hill-Sach's lesion. There is peristant capelar ederra but no detenation peragenced cyst.

Normal supraphatus intrapinatus form mince and subcapulatis tandon complieses. There is a Type II morphology of the lateral acronial arch(curved undersurface). There is perligamenus fluid extending along the occeamediai ligament.

Normal acerniocular articulation

IMPRESSION
Posterior lateral four ingivirg hte posterior band of the interior glenoumai ligament as discussed above.

FIG. 5

FIND MESSAGES

MESSAGE SEARCH

MESSAGE ID

ACCESSION NUMBER

DELIVERY STATUS
DELIVERED

NPI

RECIPIENT FIRST NAME

RECIPIENT LAST NAME

RECEIVED FROM (CT)
3/30/2015 12:00:00 AM

RECEIVED TO (CT)
3/30/2015 11:59:59 PM

DELIVERY NETWORK
ALL

DELIVERED FROM (CT)

DELIVERED TO (CT)

ACCOUNTS
SELECT CUSTOMER

LOCATIONS
--SELECT--

RECORDS PER PAGE
20

MAXIMUM RESULTS
500

SEARCH

SEARCH RESULTS 1 - 20 OF 58

| Received (Central Time) | Recipient | Status | Delivery Type | Delivery Network | Delivered (Central Time) | Customer Name | Location |
|---|---|---|---|---|---|---|---|
| 3/30/2015 11:59:16 AM | Jason Barrett | Delivered | Electronic | Surescripts | 3/30/2015 11:59:17 AM | ICN 3.3 PQA With RIS 8.1 | Beachside |
| 3/30/2015 11:37:57 AM | Jason Barrett | Delivered | Electronic | Surescripts | 3/30/2015 11:38:59 AM | ICN 3.3 PQA With RIS 8.1 | Beachside |
| 3/30/2015 10:53:00 AM | Jason Barrett | Delivered | Electronic | Surescripts | 3/30/2015 10:53:02 AM | Customer 1869 | Beachside |

FIG. 14

FIND USAGE REPORTS
AUDIT

USAGE REPORT SEARCH

* USAGE REPORT FOR
CLINICAL REPORTS

* FROM DATE (CT)
03/01/2015

* TO DATE (CT)
03/29/2015

** Please note the search results will NOT include today's usage information.

SEARCH

SEARCH RESULTS 31 - 35 OF 35

| Customer Name | Location | IFS Num | Delivery Method | Num of Messages | Delivery Network | Message to Ref.Physicians | Num of Copies |
|---|---|---|---|---|---|---|---|
| greatcustomer | greatlocation | greatcustomer | Electronic | 2 | Surescripts | 0 | 2 |
| greatcustomer | greatlocation | greatcustomer | Fax | 2 | Surescripts | 2 | 0 |
| Customer with Automap | | 8888 | Electronic | 1 | Surescripts | 1 | 0 |
| Customer for 1798 | Beachside | 1798 | Electronic | 1 | Surescripts | 1 | 0 |
| Customer for 1798A | Beachside | 1798A | Electronic | 1 | Surescripts | 1 | 0 |

<< 1 2 3 4

EXPORT

FIG. 23 iConnect Network® ▪Image Viewing | +CREATE ORDER | ✎ Batch Sign | Find Patient 🔍 | 🕒 Hello, David

BRANDON MARSHALL ▪

ORDER#: 0980980
ORDER DATE: 2/22/14

STATUS:
AWAITING SIGNATURE

Personal Info          Body Part          ✎EDIT
DOB: 1/28/72              Back
Gender: Male
Contact: 555.312.1234     Reason
SSN: ###-##-####          Severe Pain
Address:
123 Sheridan RD.          Diagnosis
Wilmette, IL 60091        Fractured Spine

Referring Physician Info   Exam
Dr. David Chamberlain          MRI Spine W/O Contrast
1234 Washington Ave, Suite 200
Chicago, IL 60601              Clinical Notes
(312)555-1234                  Patient is allergic to text on
NPI: 000000000                 a webpage
Tax ID: 00000000

Insurance Provider
Land of Lincoln
Group #: 01234557
ID #: XY577845

Attachments
CDA

🏥 NorthShore
NorthShore University HealthSystem
200 W. Wacker DR Suite 1450
Chicago IL 60601
(555) 847.1234

By entering your password on this
form, you are affirming that you are
a qualified and licensed medical
professional and are authorized to
issue orders for radiological
procedures by state law.

REFERRING PHYSICIAN
USERNAME
[ dchamberlain ]

PASSWORD
[ ********** ]

NOTES/COMMENTS (optional)
[                    ]

[ ✎SIGN ORDER ]

| iConnect Network® | ▤ View Orders | 88 Assignments | | | Find Patient 🔍 | 👤 Hello, Mary |
|---|---|---|---|---|---|---|
| Sort By ▼ | Filter by Status ▼ | ⚙ | | | | |
| MARSHALL, Brandon | ⚑ | Order Date: 01/15/2014 | Chicago Northside MRI | Awaiting Pre-Auth In Process | | ▤ VIEW ORDER |
| ROSE, Pete | ⚑ | Order Date: 01/15/2014 | Southwest Diagnostics | Awaiting Pre-Auth | | ▤ VIEW ORDER |
| VONN, Lindsey | ⚑ | Order Date: 01/15/2014 | Chicago Northside MRI | Awaiting Pre-Auth | | ▤ VIEW ORDER |
| KERRIGAN, Nancy | | Order Date: 01/15/2014 | Southwest Diagnostics | Awaiting Pre-Auth | | ▤ VIEW ORDER |
| JORDAN, Michael | | Order Date: 01/15/2014 | Chicago Northside MRI | Awaiting Pre-Auth In Process | | ▤ VIEW ORDER |
| WHITE, Shaun | | Order Date: 01/15/2014 | Chicago Northside MRI | Awaiting Pre-Auth | | ▤ VIEW ORDER |
| SORENSTAM, Annika | | Order Date: 01/15/2014 | Southwest Diagnostics | Awaiting Pre-Auth | | ▤ VIEW ORDER |
| WATSON, Bubba | | Order Date: 01/15/2014 | Radiology, LTD. | Awaiting Pre-Auth | | ▤ VIEW ORDER |
| MCGWIRE, Mark | | Order Date: 01/15/2014 | Radiology, LTD. | Awaiting Pre-Auth | | ▤ VIEW ORDER |
| WIE, Michelle | | Order Date: 01/15/2014 | Chicago Northside MRI | Authorized | | ▤ VIEW ORDER |
| MILLER, Bode | | Order Date: 01/15/2014 | Southwest Diagnostics | Authorized | | ▤ VIEW ORDER |
| PIPPEN, Scottie | | Order Date: 01/15/2014 | Southwest Diagnostics | Denied | | ▤ VIEW ORDER |
| SOSA, Sammy | | Order Date: 01/15/2014 | Chicago Northside MRI | Missing Info | | ▤ VIEW ORDER |

FIG. 25

METHODS AND SYSTEMS FOR ROUTING IMAGE REPORTS

RELATED APPLICATIONS

This application claims priority to U.S. Provisional Application No. 61/973,728 filed Apr. 1, 2014, the entire content of which is incorporated by reference herein.

FIELD

Embodiments of the present invention relate to methods and systems for managing image studies within the medical industry.

BACKGROUND

When medical images are collected as part of an imaging procedure, the images (referred to as an image study) are provided to a radiologist or other "reading physician" for review. The radiologist generates a report containing the radiologist's findings based on review of the images. Traditionally, the findings of the report are faxed to the physician who ordered the imaging procedure. The fax includes only the text-based findings and not the images.

SUMMARY

In some situations, the ordering physician may want to see the images associated with the report (e.g., to verify the findings or better understand the meaning of the findings). The images, however, may be stored in a picture archiving and communication system ("PACS") that may or may not be readily accessible to the physician. Also, given the size of the images and the fact that the physician does not always want to review the images, it is impractical to send the images to the physician with the report.

Therefore, embodiments of the invention provide systems and methods for connecting an ordering physician with completed image reports and access to images and related reports. Embodiments of the invention also provide systems and methods for connecting an ordering physician with an imaging provider for placing an order for an imaging procedure. In addition, embodiments of the invention provide systems and methods for tracking the status of an order (e.g., whether an order is scheduled, complete, undergoing a pre-authorization process, etc.) and generating reports regarding orders and/or reports. Furthermore, embodiments of the invention provide systems and methods for managing a pre-authorization process for an order.

One embodiment of the invention includes at least one server that sits between a report source (e.g., a radiology information system) and a report destination (e.g., an ordering physician's electronic medical record ("EMR") system). The server routes reports from the report source to the report destination. In some embodiments, the server routes the report using a third-party network, such as a clinical messaging network. The server can access a directory to identify how to route a particular report to a particular ordering physician. The server also embeds a link in a routed report. The ordering physician can click on the link to access a set of images associated with the report. For example, when an ordering physician (or other individual obtaining the report with the link) clicks the link, the ordering physician accesses the server via a browser application, the server identifies the image set associated with the link, the server identifies where the image set is stored, and the server automatically transfers the ordering physician to an image viewer where he or she can access the stored image set. In some embodiments, the server also authenticates the ordering physician before transferring the ordering physician to the image viewer. In some embodiments, the server also allows a user to place an order of an imaging procedure. Furthermore, in some embodiments, the server allows a user to track and/or perform a pre-authorization process for an order.

For example, one embodiment of the invention provides a method of managing an image study. The method includes receiving, with a server, a completed report for the image study from a report source, establishing, with the server, a unique identifier for a set of images associated with the completed report and stored in an image repository accessible through an image viewer, storing, with the server, the unique identifier and an identifier of the image viewer in an image directory, and automatically, with the server, creating a link associated with the completed report, the link based on the unique identifier. The method also includes identifying, with the server, a report destination for the completed report, and transmitting, with the server, the completed report and the link to the report destination. In addition, the method includes, when a recipient selects the link, automatically, with the server, identifying the image viewer based on the image directory, and automatically, with the server, providing the recipient with access to the image viewer.

Another embodiment of the invention provides a system for managing an image study. The system includes a server configured to communicate with a report source over at least one network connection. The server is configured to receive a completed report for the image study from the report source, establish a unique identifier for a set of images associated with the completed report and stored in an image repository accessible through an image viewer, store the unique identifier and an identifier of the image viewer in an image directory, and automatically create a link associated with the completed report, the link based on the unique identifier. The server is also configured to identify a report destination for the completed report and transmit the completed report and the link to the report destination. In addition, when a recipient selects the link, the server is configured to automatically identify the image viewer based on the image directory automatically provide the recipient with access to the image viewer.

Yet another embodiment of the invention provides a method of managing an image study. The method includes receiving, with a server, order information for an imaging procedure from a referring physician through a user interface remotely accessible over a network connection, and automatically, with the server, routing the order information to a report source. The method also includes receiving, with the server, order status information from the report source, and making, with the server, the order status information available to the referring physician through the user interface. The method further includes receiving, with the server, a completed report for the imaging procedure from the report source, making, with the server, the completed report available to the referring physician through the user interface, and making, with the server, a set of images associated with the completed report available to the referring physician.

Still another embodiment of the invention provides a system for managing an image study. The server is configured to communicate with a report source and includes a portal providing access to user interfaces accessible over at least one network connection. The server is also configured to receive order information for an imaging procedure from a referring physician through the portal and automatically route the order information to the report source. In addition, the server is configured to receive order status information from the report source and make the order status information available to the referring physician through the portal. Furthermore, the server is configured to receive a completed report for the imaging procedure from the report source, make the completed report available to the referring physician through the user interface, and make a set of images associated with the completed report available to the referring physician.

A further embodiment of the invention provides a method of managing an image study. The method includes identifying, with a server, an order for an imaging procedure requiring insurance pre-authorization, displaying, with the server, the order to a first user through a user interface remotely accessible over a network connection, and receiving, with the server, an assignment of the order to a second user from the first user. The method also includes displaying, with the server, the order to the second user through the user interface, displaying, with the server, a plurality of tasks for obtaining the insurance pre-authorization for the order to the second user through the user interface, wherein one of the plurality of tasks includes receiving a pre-authorization code for the order, and tracking, with the server, completion of each of the plurality of tasks by the second user through the user interface. In addition, the method includes providing, with the server, information regarding the completion of each of the plurality of tasks to the first user through the user interface.

Another embodiment of the invention provides a system for managing an image study. The system includes a server configured to communicate with a report source and includes a portal providing access to user interfaces accessible over at least one network connection. The server is also configured to identify an order for an imaging procedure requiring insurance pre-authorization, display the order to a first user through the portal, and receive an assignment of the order to a second user from the first user through the portal. The server is also configured to display the order to the second user through the portal, display a plurality of tasks for obtaining the insurance pre-authorization for the order to the second user through the portal, wherein one of the plurality of tasks includes receiving a pre-authorization code, and track completion of each of the plurality of tasks by the second user through the portal. In addition, the server is configured to provide, through the portal, information regarding the completion of each of the plurality of tasks to the first user.

Other aspects of the invention will become apparent by consideration of the detailed description and accompanying drawings and appendices.

BRIEF DESCRIPTION OF THE DRAWINGS

FIG. 3 is a screen shot illustrating a user interface, provided by the report source included in the system of FIG. 1A, for tracking completed image reports transmitted by the report source.

FIGS. 5 and 6 are a completed image report provided to the report destination included in the system of FIG. 1A.

FIG. 14 is a screen shot illustrating a user interface, provided by the routing server included in the system of FIG. 1A, for allowing a user to query for details regarding one or more reports handled by the routing server.

FIG. 16 is a screen shot illustrating a user interface, provided by the routing server included in the system of FIG. 1A, displaying a usage report for the routing server.

FIGS. 18-23 are screen shots illustrating a user interface, provided by the routing server included in the system of FIG. 17, for obtaining order information.

FIGS. 24 and 25 are screen shots illustrating a user interface, provided by the routing server included in the system of FIG. 17, for providing order status information.

DETAILED DESCRIPTION

Figure 1A:
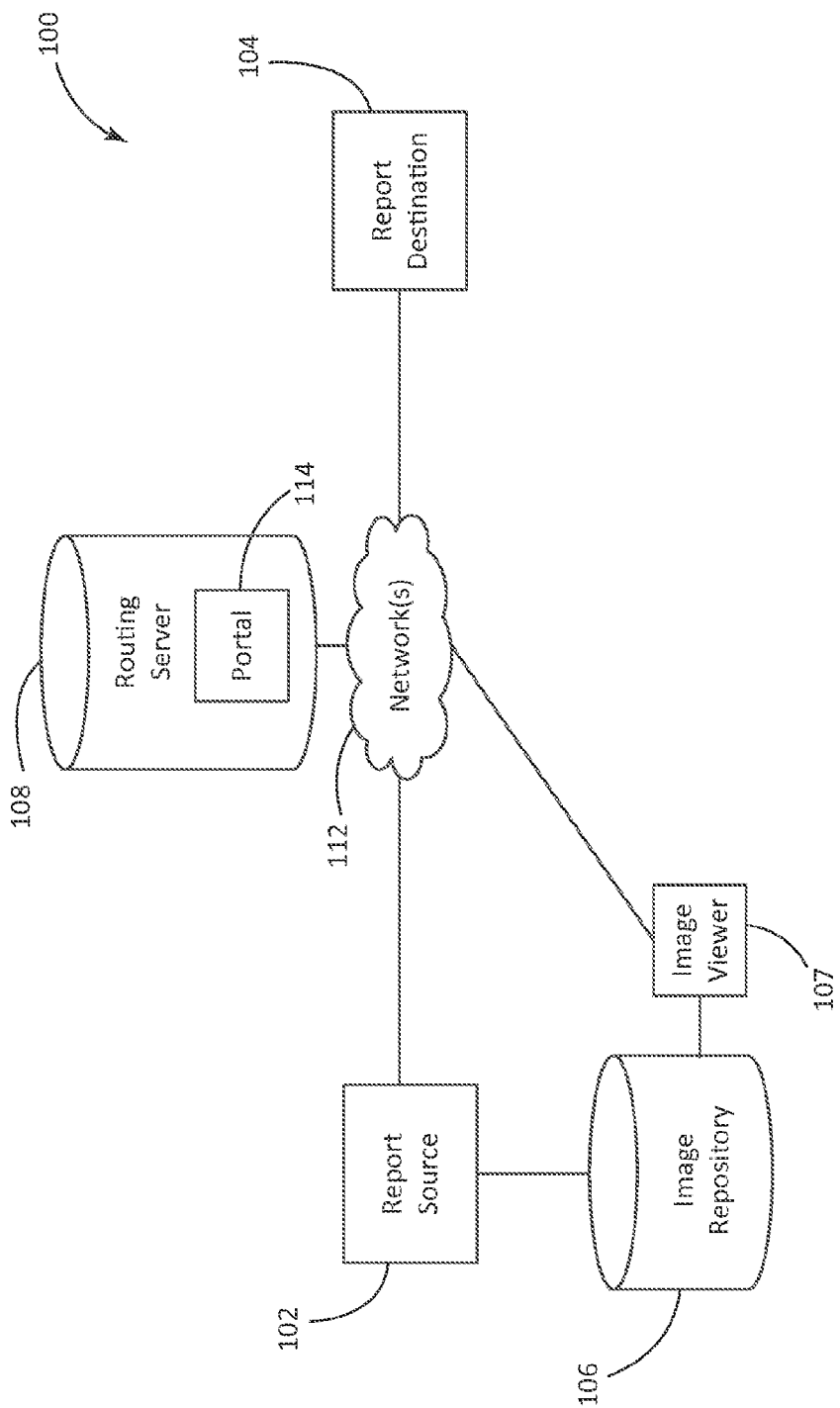
FIG. 1A schematically illustrates a system for routing image reports from a report source to a report destination.

Before any embodiments of the invention are explained in detail, it is to be understood that the invention is not limited in its application to the details of construction and the arrangement of components set forth in the following description or illustrated in the accompanying drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. Also, electronic communications and notifications may be performed using any known means including secure email, direct connections, wired connections, wireless connections, etc. It should also be noted that a plurality of hardware- and software-based devices, as well as a plurality of different structural components may be utilized to implement the invention. Furthermore, and as described in subsequent paragraphs, the specific configurations illustrated in the drawings are intended to exemplify embodiments of the invention, it being understood that other alternative configurations are possible.

It should also be noted that embodiments of the invention may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects of the invention may be implemented in software (e.g., stored on non-transitory computer-readable medium) executable by one or more processing units. As such, and by way of example, "electronic devices," "computers," "computing devices," "controllers," "control devices," or "control modules" described in the present specification can include one or more processing units, one or more computer-readable medium modules, one or more input/output interfaces, and various connections (e.g., a system bus) connecting the components.

Report Routing

FIG. 1A illustrates a system 100 for communicating completed image reports from a report source 102 to a report destination 104. In some embodiments, the report source 102 includes a radiology information system ("RIS") operated by an imaging provider. In other embodiments, the report source 102 can include a picture archiving and communication system ("PACS"), an electronic medical record ("EMR") system, a dictation system, a cloud storage system, a hospital information system ("HIS"), etc.

The report source 102 stores image reports. An image report includes findings by a radiologist based on a set of images (i.e., an image study) generating during an imaging procedure. The image studies are generally stored in a separate image repository 106, such as an on-premise picture archiving and communication system ("PACS") or a cloud storage environment. In some embodiments, the image repository 106 can be operated by the entity that operates the report source (e.g., an imaging provider). However, in other embodiments, the image repository 106 can be operated by a different entity. Also, in some embodiments, the image repository 106 can be included in the report source 102.

An image viewer 107 is associated with the image repository 106, which allows users to access stored images through a user interface remotely accessible over a network connection, such as a web page accessible over the Internet through a browser application. For example, the image viewer 107 can include a web server that authenticates users accessing the web server over the Internet through a browser application and, when authenticated, allows users to access and view images stored in the associated image repository 106. In some embodiments, the image viewer 107 is a zero-footprint image viewer that only requires a browser application to access and view images. In other embodiments, however, the image viewer 107 can include a dedicated interface or connection between the image repository and the routing server 108 described below. It should be understood that, in some embodiments, the report source 102 stores image studies to more than one image repository 106. Also, in some embodiments, the image viewer 107 is provided as part of the image repository 106, as compared to a separate device as illustrated in FIG. 1A.

The report destination 104 can include a system associated with a recipient of a completed report, such as the physician initially ordering the imaging procedure (i.e., the "ordering physician"). In some embodiments, the report destination 104 includes an EMR system accessible to the recipient. However, in other embodiments, the report destination 104 includes an HIS, an email server, a cloud storage environment, etc.

Figure 1B:
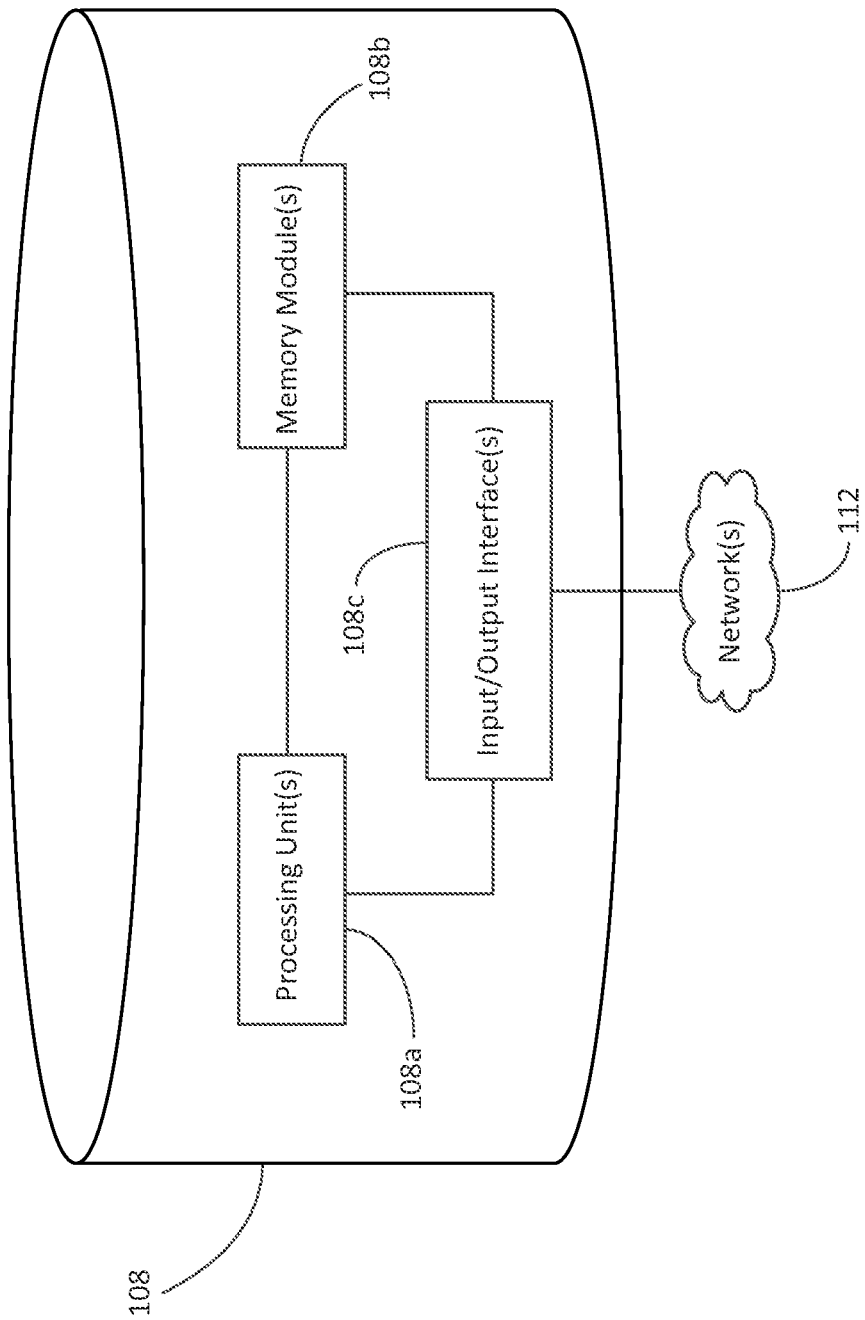
FIG. 1B schematically illustrates a routing server included in the system of FIG. 1A.

The system 100 also includes a central hub or routing server 108. As illustrated in FIG. 1B, the server 108 includes one or more processing units 108a, one or more computer-readable memory modules 108b, and one or more input/output interfaces 108c. The memory modules 108b can include non-transitory memory, such as random access memory and/or read-only memory. The processing units 108a can include a microprocessor configured to execute instructions stored in the memory modules 108b. The memory modules 108b can also store data used with and generated by execution of the instructions. The input/output interfaces 108c allow the server 108 to communicate with external devices, including one or more wired or wireless networks 112 (e.g., the Internet, a clinical messaging network, a local area network, etc.). The server 108 can use the networks 112 to communicate with the report source 102, the report destination 104, and the image viewer 107 and, in some embodiments, uses different networks 112 to communicate with each device. However, in some embodiments, the server 108 can be configured to have a dedicated interface or connection to one or more devices, such as the report source 102 and/or the image viewer 107.

It should be understood that in some embodiments, the server 108 includes additional components than those illustrated in FIG. 1B. It should also be understood that, in some embodiments, the functionality provided by the server 108 as described below can be distributed among multiple servers. In addition, it should be understood that although only a single report source 102, report destination 104, and image viewer 107 are illustrated in FIG. 1A, the server 108 can be configured to communicate with multiple different report sources 102, report destinations 104, and image viewers 107.

As illustrated in FIG. 1A, the server 108 can also include a network-based user interface portal 114 that allows a user (e.g., a referring physician, a radiologist, etc.) to interact with the server 108. For example, the portal 114 can provide access to user interfaces accessible over the Internet using a browser application. It should be understood that the portal 114 can be provided by the server 108 or a separate device. Also, it should be understood that the user interfaces described herein as being provided by the server 108 can be provided by the portal 114.

Figure 1C:
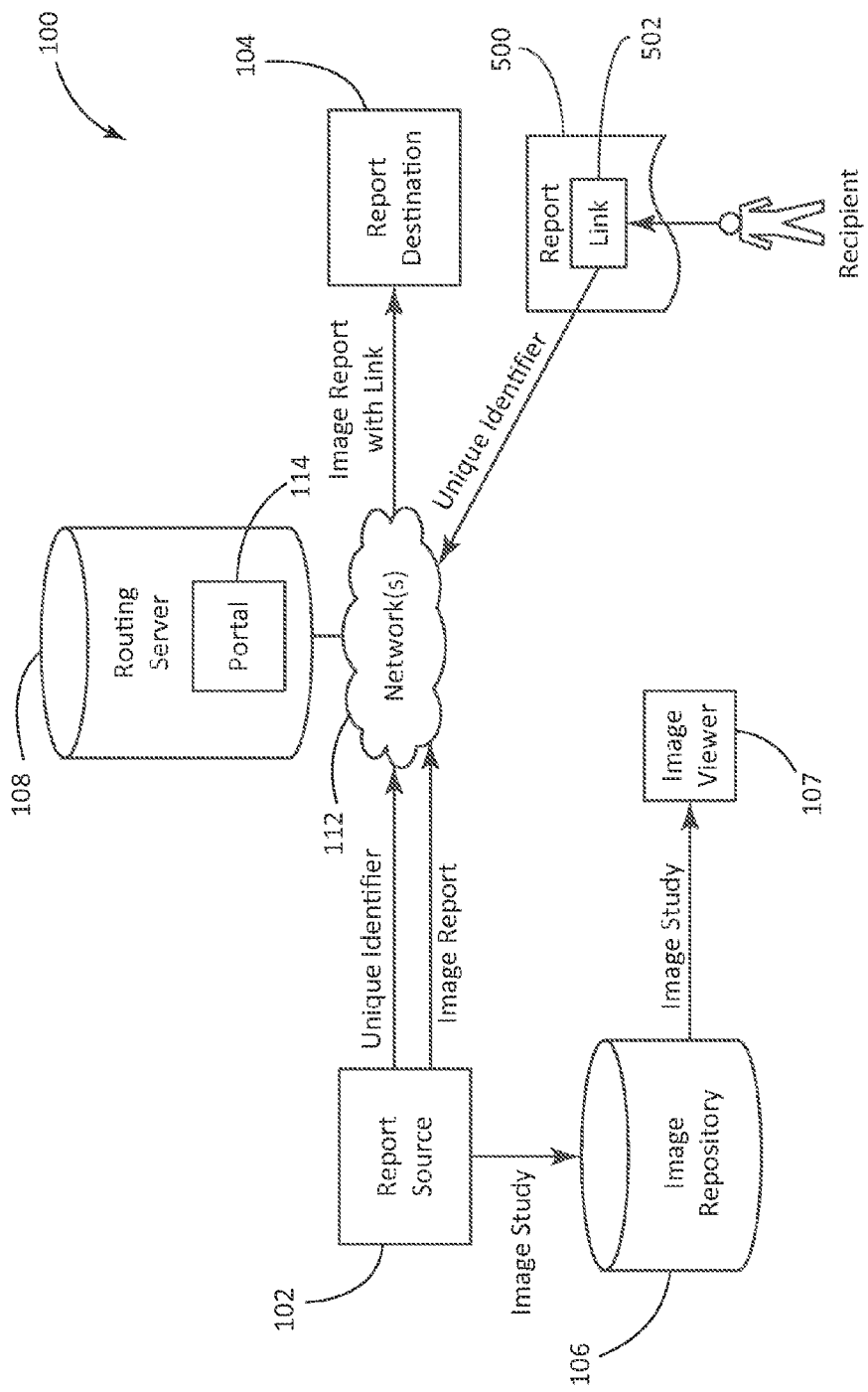
FIG. 1C schematically illustrates a method of routing a completed report from a report source to a report destination using the system of FIG. 1A
Figure 2:
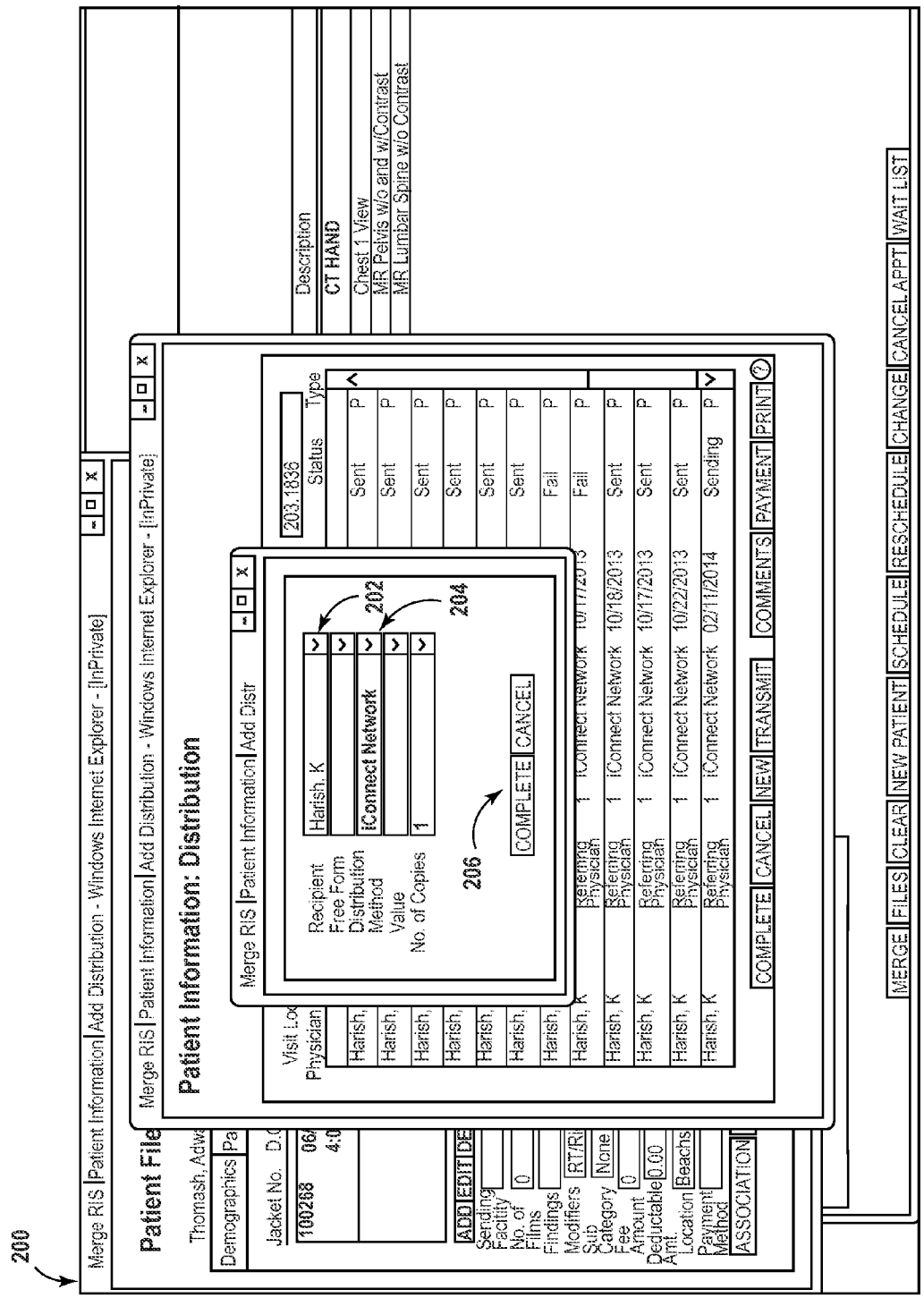
FIG. 2 is a screen shot illustrating a user interface, provided by the report source included in the system of FIG. 1A, for manually transmitting a completed image report from the report source to the routing server included in the system of FIG. 1A.

As illustrated in FIG. 1C, when an image report is completed, the report source 102 routes the completed report to the server 108. The report source 102 can be configured to automatically route a completed report to the server 108. Alternatively or in addition, the report source 102 can be configured to allow a user to manually initiate transfer of the report. For example, FIG. 2 illustrates a user interface 200 provided by the report source 102. As illustrated in FIG. 2, the user interface 200 allows a user to specify one or more recipients for a completed report (e.g., the ordering physician) using a "Recipient" input mechanism 202. The user interface 200 also allows a user to specify a distribution method for the report using a "Distribution Method" input mechanism 204. For example, a user can use the "Distribution Method" input mechanism 204 to select an identifier of the routing server 108 (e.g., "iConnect Network") when the server 108 is going to route or distribute the completed report. In some embodiments, rather than selecting the routing server 108, a user can use the "Distribution Method" input mechanism 204 to specify an alternative delivery method, such as fax transmission or a mail delivery (e.g., performed directly by the report source 102). As illustrated in FIG. 2, a user can select a "Complete" selection mechanism 206 to manually initiate transmission of the report. In some embodiments, although the report source 102 transmits a completed report to the server 108, the report source 102 retains a copy of each completed report.

As illustrated in FIG. 1C, the report source 102 also transmits a unique identifier for the image study associated with the completed report (stored in the image repository 106). In some embodiments, the unique identifier includes an accession number assigned to the image study. It should be understood that, in some embodiments, the report source 102 transmits the unique identifier within the completed report transmitted to the server 108 rather than as a separate transmission. Also, it should be understood that the unique identifier provided by the report source 102 can include one or more pieces of identifying information for the image study and associated report, such as an accession number, a report identifier, a report source identifier, a patient identifier, an image repository identifier, etc.

Figure 3:
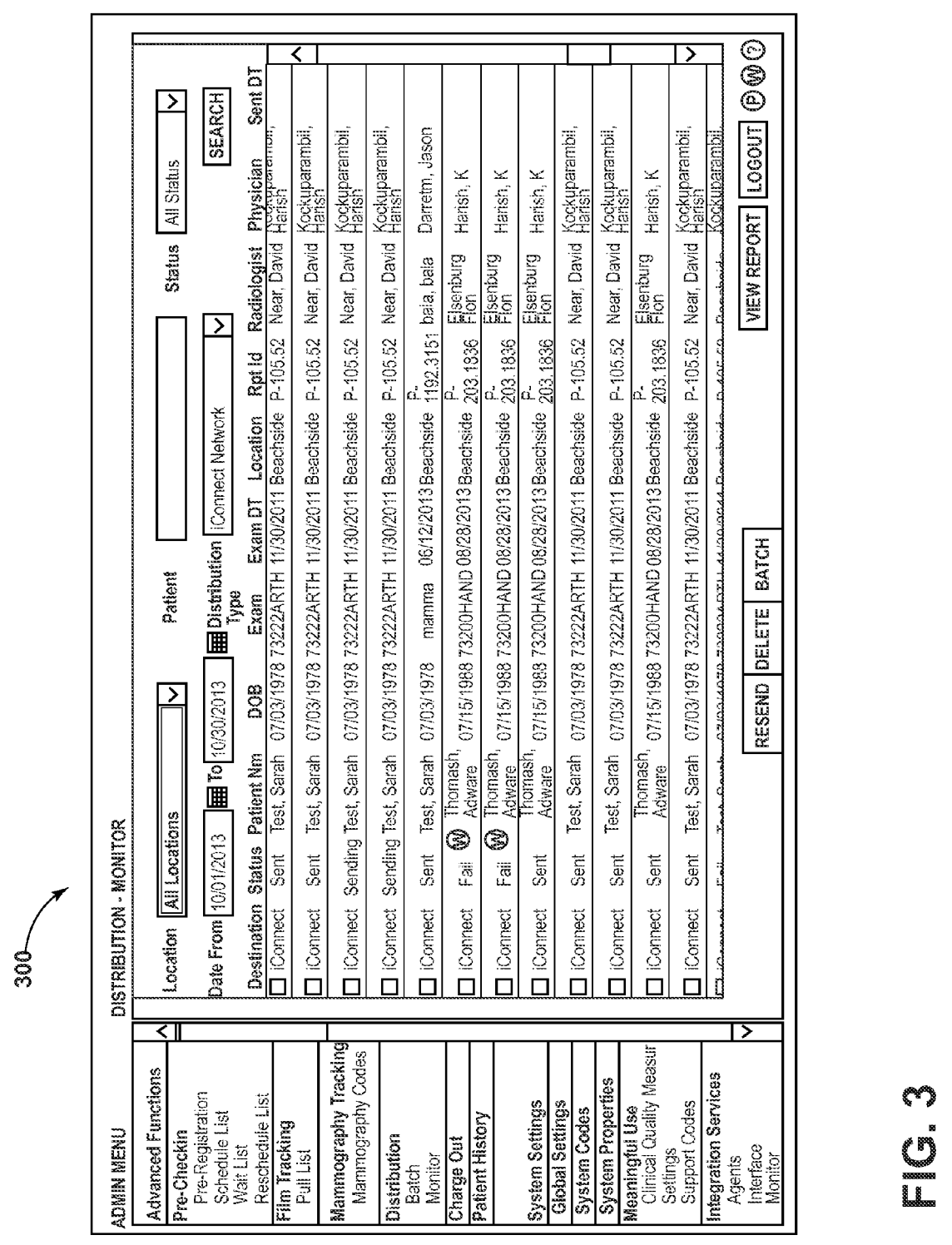

In some embodiments, the report source 102 tracks distributed completed reports. For example, as illustrated in FIG. 3, the report source 102 can provide a user interface 300 that displays a list of reports transmitted from the report source 102. A user can use the interface 300 to identify what reports were transmitted and how each report was transmitted (e.g., to the routing server 108, via fax, etc.). As illustrated in FIG. 3, the interface 300 can also specify a report status, such as whether a report was successfully delivered. In particular, the interface 300 can indicate whether a report was successfully transmitted to the routing server 108 and/or the associated recipient (i.e., the report destination 104).

The server 108 uses information in the received report, the unique identifier, or other information transmitted from the report source 102 (e.g., a recipient selected by the user using the interface 200 illustrated in FIG. 2) to identify one or more recipients for the completed report (e.g., the ordering physician and, optionally, other physicians or specialists). For example, in some embodiments, a completed report includes an identifier of one or more recipients (e.g., a unique identifier, a name, an office or location, or a combination thereof). Also, in some embodiments, as described below, the server 108 can store original order information associated with the completed report, and the order information can include a list of one or more recipients. Accordingly, in these situations, the server 108 can match a received report to the corresponding order information (e.g., by an order number) to identify one or more recipients for the completed report.

After identifying one or more recipients for a completed report, the server 108 accesses a recipient directory to identify how to route the report to each recipient. The recipient directory can be stored on the server 108 or on a separate device accessible to the server 108. The recipient directory can specify, for each of a plurality of recipients, a method for delivering a report to the recipient. In particular, the directory can specify that a completed report should be faxed or mailed to a particular recipient and can provide a fax number or a mailing address of the recipient. Alternatively, the recipient directory can specify that a completed report should be electronically delivered to a particular recipient. For example, the recipient directory can specify that a completed report for a specific recipient should be delivered to a report destination 104 (e.g., an EMR system) associated with the recipient that is accessible over a network managed by a healthcare provider organization (e.g., Athenahealth, Allscripts, etc.) or a network managed by a third-party organization (e.g., Surescripts that provides a clinical messaging network for managing and routing messages, such as prescription-related messages). Accordingly, in these situations, the recipient directory can specify an identifier of the report destination 104 and an identifier of the network through which the report destination 104 is accessible. In some embodiments, these networks use direct messaging to securely (e.g., HIPAA-compliant and encrypted using private and public security keys, passwords, and credentials) transmit the report to a report destination 104, such as a recipient's EMR system or other device with a direct messaging address. In some embodiments, the recipient directory can also specify that a completed report for a particular recipient should be sent as an attachment to an email message and can provide an email address.

In some embodiments, the recipient directory can also specify multiple ways to route a completed report to a particular recipient and, optionally, a hierarchy for the different routing options. For example, the recipient directory can specify that electronic delivery should be initially attempted for a particular recipient. However, the recipient directory can specify that a fax and then a paper mailing, in that order, can be used if the electronic delivery fails.

The server 108 also has access an image directory that tracks where images associated with completed reports are stored. The image directory can be stored on the server 108 or on a separate device accessible by the server 108. The image directory can map the unique identifier of an image study (e.g., the accession number) to an identifier of the associated image viewer 107 through which the image study can be accessed. Alternatively or in addition, the image directory can map an identifier of an image repository 106 to the associated image viewer 107. In some embodiments, the report source 102 provides an identifier of the associated image viewer 107 or image repository 106 with the completed report, which the server 108 can use to create an entry in the image repository. In other embodiments, the server 108 can be configured to associate the unique identifier received from a particular report source 102 to the same imaging repository 106 and/or image viewer 107. Therefore, in these situations, the report source 102 does not need to provide this information to the server 108 with a completed report.

The server 108 also creates a link (e.g., a uniform resource locator ("URL")) that identifies the image study associated with the report. In some embodiments, the link is based on (e.g., includes) the unique identifier provided by the report source 102. However, in other embodiments, the link is based on (e.g., includes) a separate unique identifier generated by the routing server 108. For example, the routing server 108 can be configured to generate a unique identifier for each received report (i.e., for each image study associated with a received report). The generated unique identifier can include a sequential number generated by the server 108, which the server 108 stores with the unique identifier provided by the report source 102. In other embodiments, the generated unique identifier includes a combination of portions of the unique identifier provided by the report source 102 (e.g., accession number combined with patient identifier). Also, in some embodiments the server 108 uses other data relating to the completed report or the associated image study to establish the unique identifier (i.e., in addition to any portion of the unique identifier provided by the report source 102), such as an identifier of the image viewer 107 through which the image study can be accessed.

After creating the link, the server 108 transmits the completed report and the link to the recipient. In some embodiments, the server 108 transmits the completed report and the link as separate files. For example, the server 108 can transmit the link as an email message, text file, etc. Alternatively or in addition, as illustrated in FIG. 1C, the server can 108 embed the link into the completed report. Thus, it should be understood that the "completed report" transmitted by the server 108 as described in the present application can include the report and the associated link as separate pieces of data (e.g., separate files), the report with the link embedded therein, or a combination thereof.

Based on the data stored in the recipient directory, the server 108 can transmit the completed report by faxing or mailing a hard copy of the report to the recipient. Alternatively or in addition, the server 108 can transmit the completed report to the recipient by transmitting the completed report to the report destination 104, which can include an email server, an EMR, a HIS, a cloud storage environment, etc. For example, the server 108 can be configured to transmit the completed report to a network managed by a healthcare provider organization or a third-party organization (e.g., a clinical messaging network). The network then delivers the completed report to the report destination 104 (e.g., an EMR), where the completed report is stored and accessible by the recipient. When the report destination 104 includes an EMR or other patient-information system, the report destination 104 can be configured to automatically associate the report with any other patient information already stored in the report destination 104. It should be understood that the network delivering the completed report can be configured to further process the report as part of delivering the report to the report destination 104.

In other embodiments, where email is used to deliver the completed report (i.e., the report destination 104 includes an email server), the server 108 can be configured to add the completed report as an attachment to an email message (e.g., a secure email message) sent to the recipient's email address. The recipient receiving the email can open the report attached to the email and can store or print the report (e.g., into an EMR, HIS, or other system) as desired. In some embodiments, the email message also includes the link associated with the completed report.

In some embodiments, the server 108 can be configured to send a notification to a recipient after transmitting a completed report. For example, based on information contained in the recipient directory, the server 108 can send a recipient an electronic message, such as an email message, text message, voice message, etc., that informs the recipient that the report was transmitted (e.g., faxed, mailed, emailed, transmitted to an EMR, etc.). Alternatively or in addition, the report destination 104 can send a notification.

Figure 4:
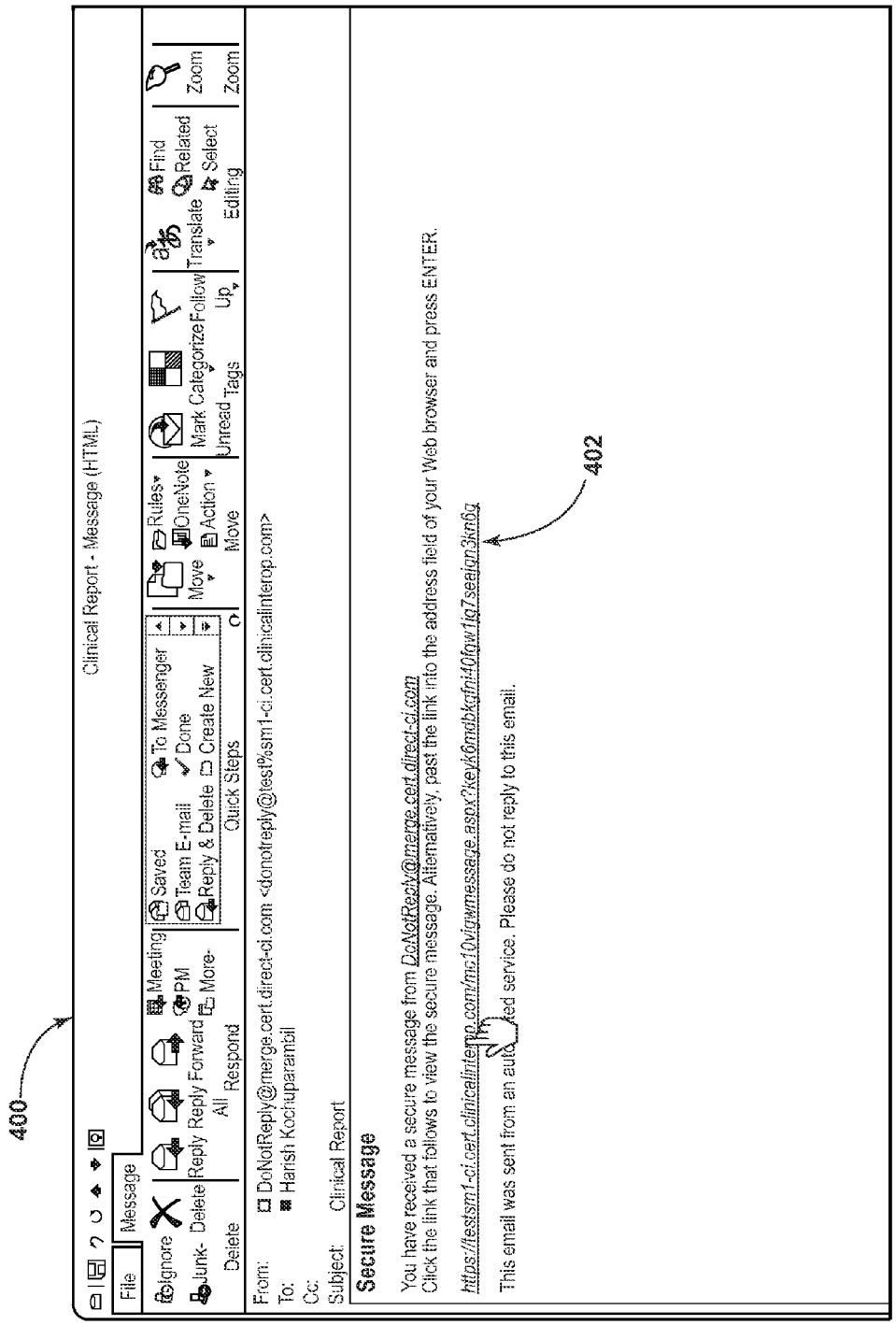
FIG. 4 is a screen shot illustrating a report received message generated by the report destination included in the system of FIG. 1A.

For example, FIG. 4 illustrates a message 400 received by a recipient informing the recipient that a report was delivered. As noted above, the message 400 can be generated by the report destination 104 and/or the server 108. As illustrated in FIG. 4, the message 400 can include a link 402 that the recipient can select (e.g., click on) to view the received report (e.g., within the report destination 104). However, in other embodiments, the report or a portion thereof can be embedded in the message 400 or included as an attachment. Also, in some embodiments, the message 400 can include the link associated with the completed report.

Figure 6:
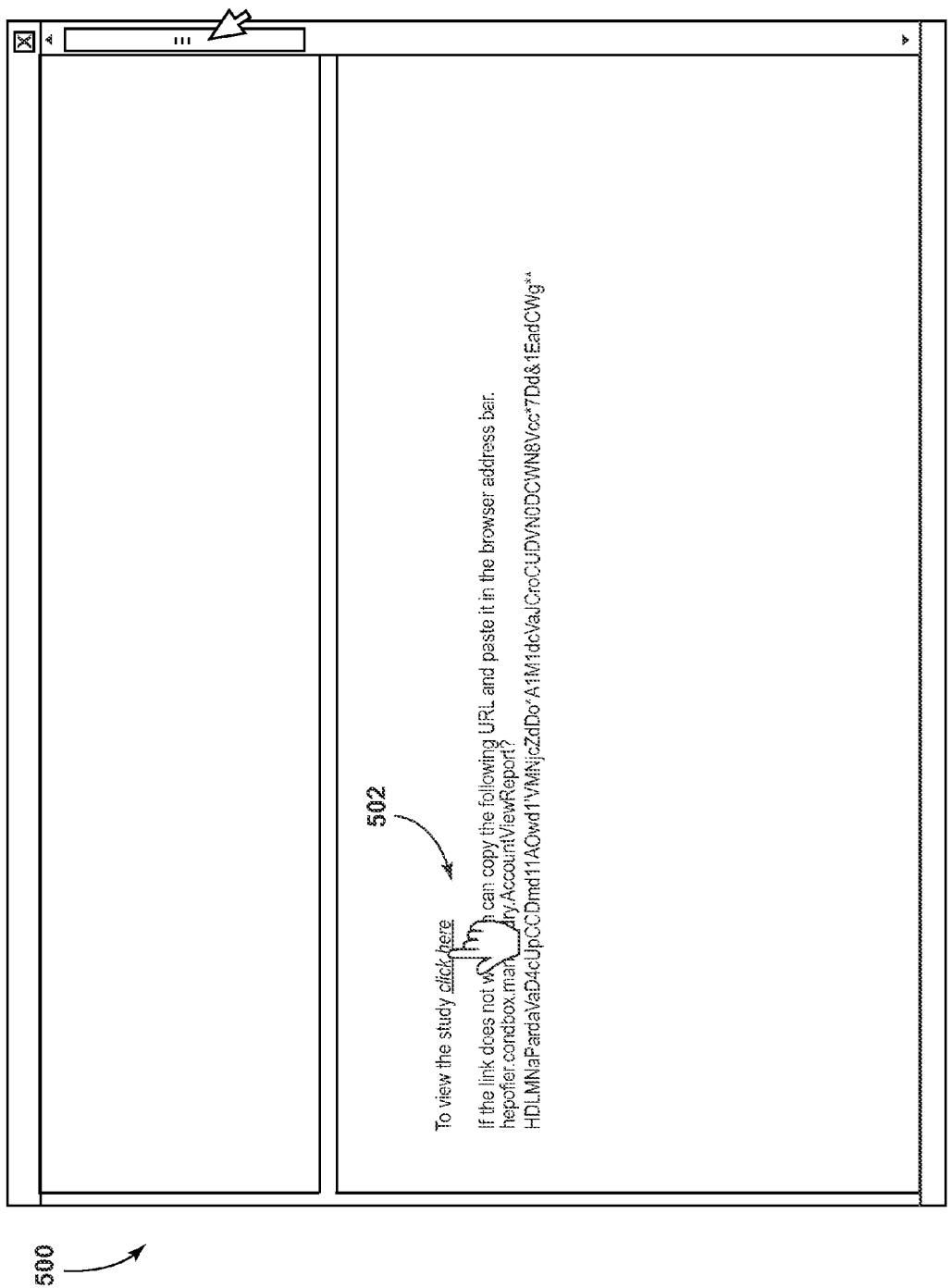

FIGS. 5 and 6 illustrate a report 500 accessible by a recipient (e.g., through clicking the link 402 included in the message 400). As illustrated in FIG. 6, the link 502 generated by the routing server 108 is embedded in the report 500. The recipient can select (e.g., click on) the link 502 to access the image study associated with the report 500. In particular, when the recipient clicks on the embedded link 502, the physician is directed to the server 108 (e.g., a web page provided by the server 108 and accessible over the Internet through a browser application). As illustrated in FIG. 1C, when the link 402 is selected, the server 108 is passed the unique identifier (i.e., the accession number) associated with the requested image study. The server 108 uses the unique identifier to identify the image viewer 107 where the requested image study is stored. In particular, the server 108 accesses the image directory and uses the unique identifier to identify the image viewer 107 through which the images can be accessed. The server 108 then provides the recipient with access to the image viewer 107.

Figure 7:
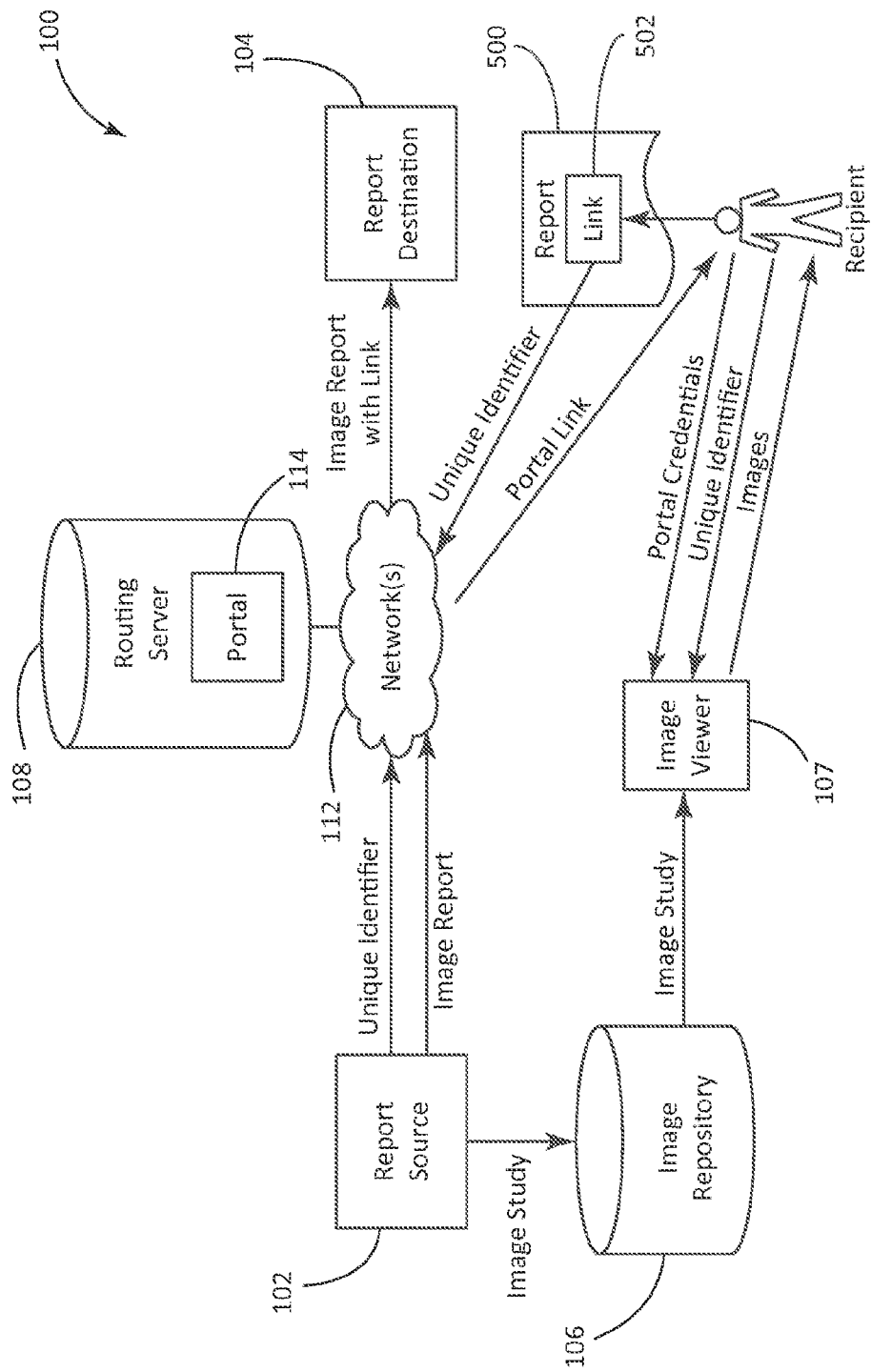
FIG. 7 schematically illustrates a method of providing a recipient of a completed report access to an associated image study using the system of FIG. 1A.

The server 108 can provide access to the image viewer 107 in one or more ways. For example, in one embodiment, as illustrated in FIG. 7, the server 108 provides access to the image viewer 107 by sending the recipient an address or link (e.g., a URL) identifying the image viewer 107. The recipient can use the link to access the image viewer 107, provide credentials (e.g., a username and password) to the image viewer 107, provide the unique identifier to the image viewer 107, and (if authorized) view one or more images included in the image study through the image viewer 107. It should be understood that, in some embodiments, the recipient can communicate with the image viewer 107 over a wired or wireless network, such as the Internet, a local area network, etc.

Figure 8:
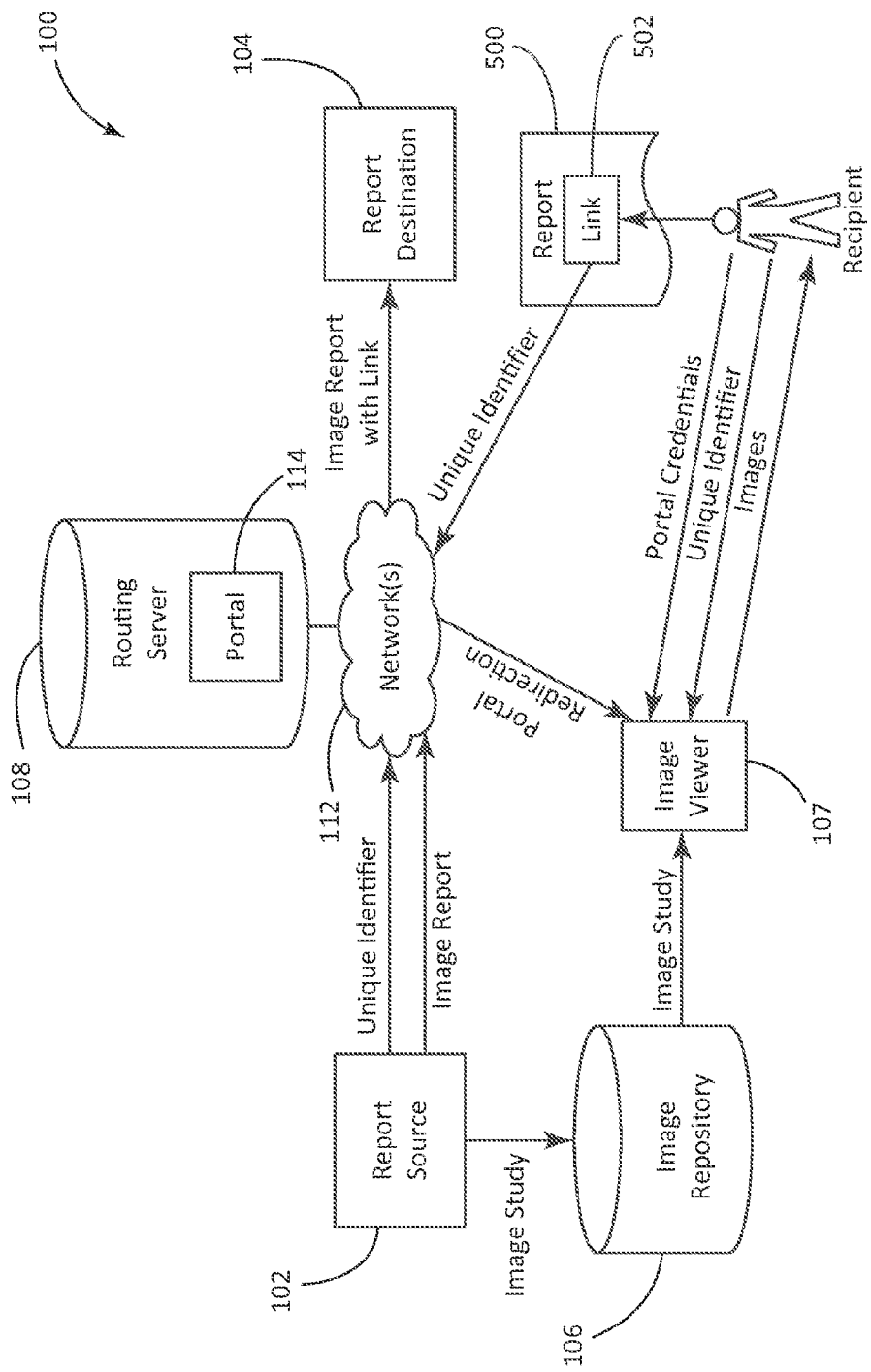
FIG. 8 schematically illustrates another method for providing a recipient of a completed report access to an associated image study using the system of FIG. 1A.

Alternatively, as illustrated in FIG. 8, the server 108 can provide the recipient with access to the image viewer 107 by automatically redirecting the recipient to the image viewer 107. After redirecting the recipient to the image viewer 107, the image viewer 107 can prompt the recipient for credentials and the unique identifier for the requested images. The image viewer 107 can then display the requested images to the recipient if the recipient's credentials are authorized.

Figure 9:
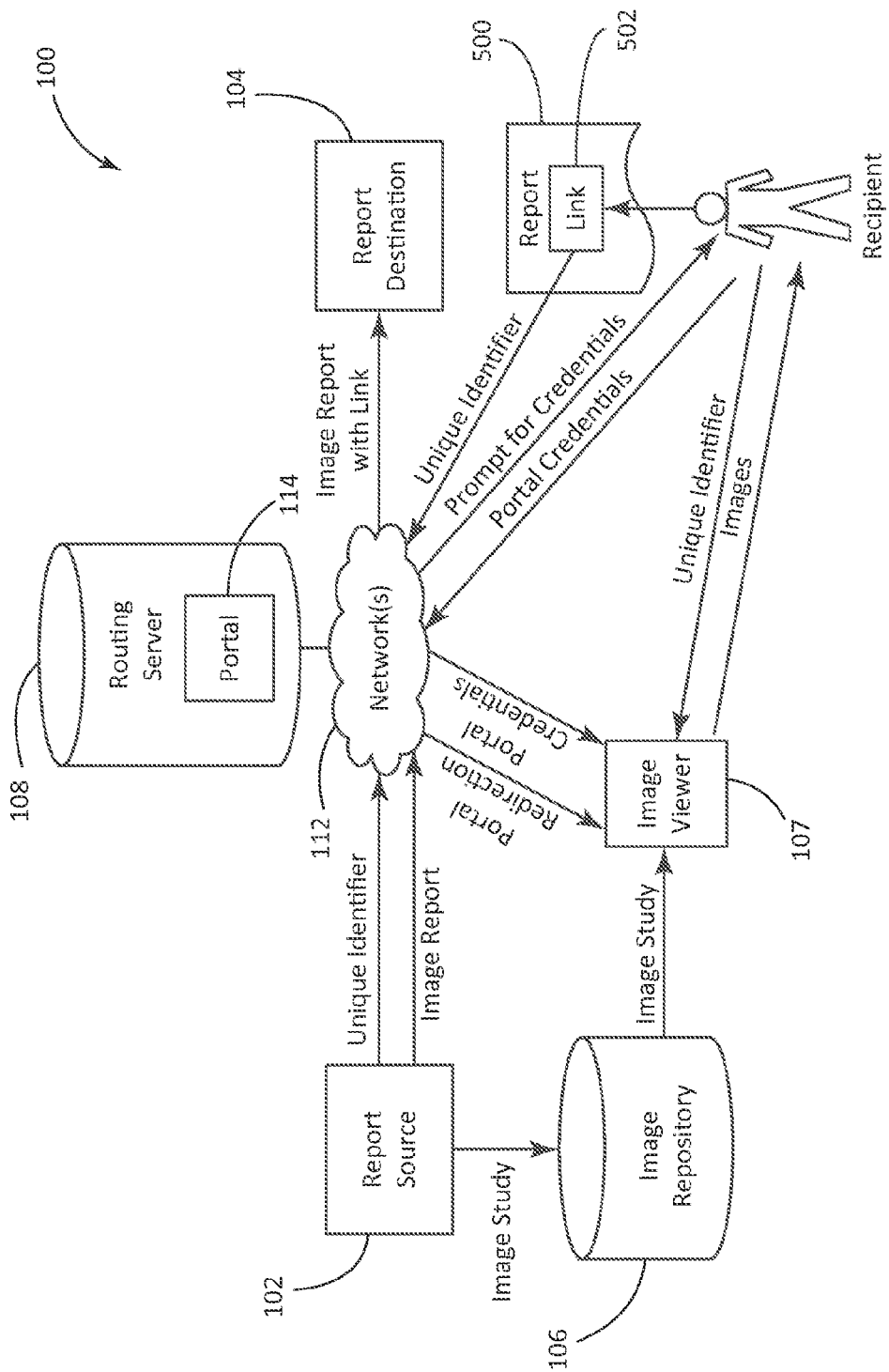
FIG. 9 schematically illustrates yet another method for providing a recipient of a completed report access to an associated image study using the system of FIG. 1A.
Figure 10:
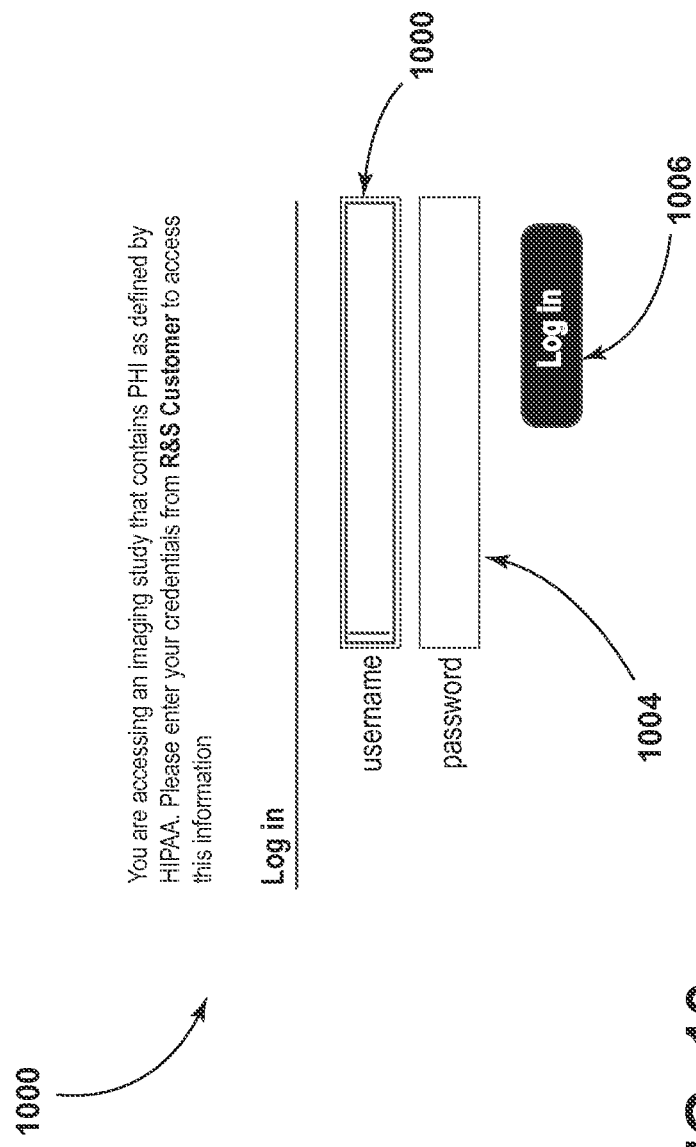
FIG. 10 is a screen shot illustrating a user interface, provided by the routing server included in the system of FIG. 1A, for prompting a recipient for credentials for accessing an image study.

Alternatively, as illustrated in FIG. 9, the server 108 can be configured to provide the recipient with access to the image viewer 107 by automatically redirecting the recipient to the image viewer 107 and automatically logging the recipient into the image viewer 107. For example, in some embodiments, the server 108 can prompt the recipient for his or her credentials for the image viewer 107 (e.g., a username and a password). For example, the server 108 can provide a user interface 1000 as illustrated in FIG. 10 that includes a "User Name" input mechanism 1002, a "Password" input mechanism 1004, and a "Log In" selection mechanism 1006. Upon receiving the recipient's credentials, the server 108 can pass the credentials to the image viewer 107 and seamlessly log the recipient into the image viewer 107. After being logged into the image viewer 107, the recipient can supply the image viewer 107 with the unique identifier, which the image viewer 107 can use to identify which image study to display for the recipient. It should be understood that in some embodiments, after logging the recipient into the image viewer 107, the server 108 can also be configured to provide the image viewer 107 with the unique identifier (as compared to having the recipient provide the identifier to the image viewer 107).

Figure 11:
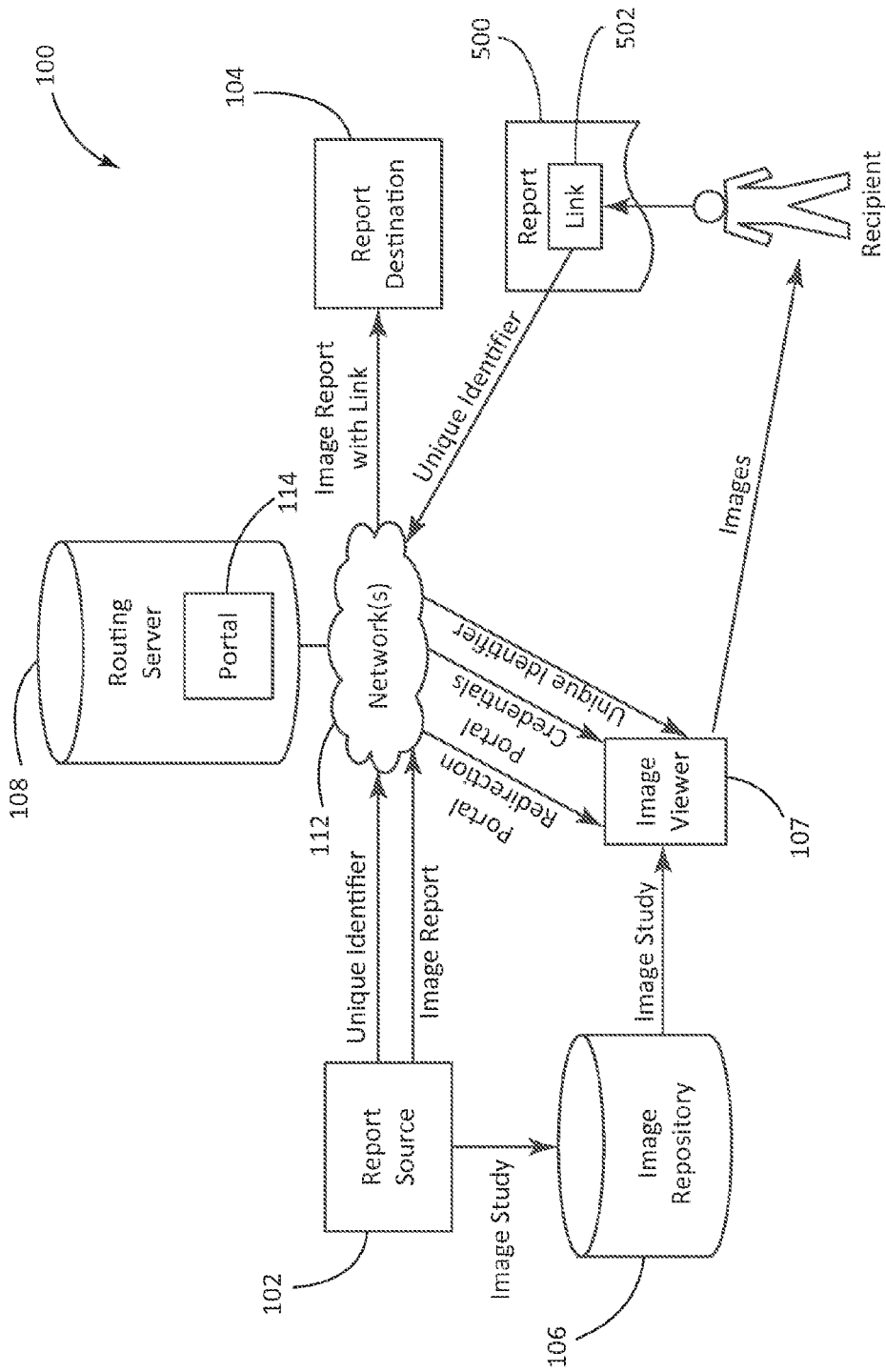
FIG. 11 schematically illustrates still another method for providing a recipient of a completed report access to an associated image study using the system of FIG. 1A.

Alternatively, as illustrated in FIG. 11, the server 108 can be configured to provide the recipient with access to the image viewer 107 by automatically redirecting the recipient to the image viewer 107 and automatically logging the recipient into the image viewer 107 without prompting the recipient for the credentials. For example, the recipient's credentials provided to the report destination 104 (e.g., for initially accessing the completed report 500) can be provided to (or stored) by the server 108. Accordingly, the server 108 can use the credentials to automatically log the recipient into the image viewer 107. In this situation, the server 108 can be configured to use the recipient's credentials for the report destination 104 as the credentials for the image viewer 107 or can be configured to look up the recipient's credentials for the image viewer 107 using the recipient's credentials for the report destination 104 or other identifying information of the recipient. Accordingly, in these embodiments, the physician can access the image study using a single sign-on (i.e., only signing into the report destination 104). After being logged into the image viewer 107, the recipient can provide the unique identifier to the image viewer 107 to access the image study. However, as illustrated in FIG. 11, to continue the seamless nature of this embodiment, the server 108 can be configured to automatically provide the image viewer 107 with the unique identifier before transferring the recipient to the image viewer 107. Therefore, in this embodiment, the recipient selects the link 502 and seamlessly views the associated images without being required to provide any intermediary or further input.

It should be understood that in any embodiment where the server 108 logs into the image viewer 107 on the recipient's behalf, the server 108 can continue to communicate with the image viewer 107 on the recipient's behalf and forward information from the image viewer 107 to the recipient, including, for example displaying images. In these situations, the server 108 acts as an interface between the recipient and the image viewer 107. For example, in some embodiments, the recipient may not have credentials for the image viewer 107, but the server 108 can have credentials for the image viewer 107, which the server 108 can use to access the requested image study (e.g., as long as the server 108 can verify the recipient and the recipient's authorization to view the requested image study).

Figure 12:
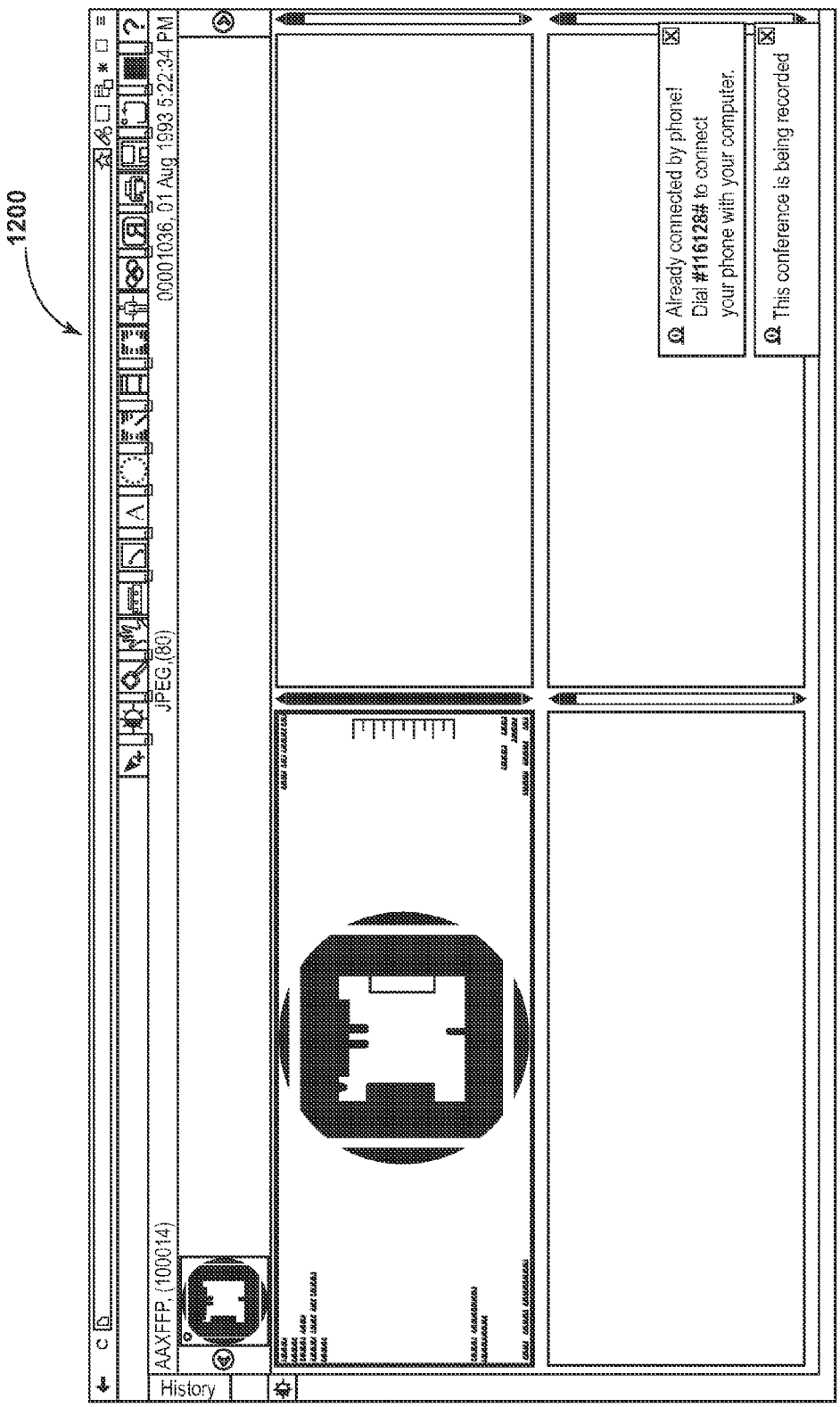
FIG. 12 is a screen shot illustrating a user interface for displaying an image study.

FIG. 12 illustrates a user interface 1200 (e.g., provided by the image viewer 107 or the server 108) that displays images of the requested image study to a recipient. As illustrated in FIG. 12, in some embodiments, the user interface 1200 allows the recipient to take certain actions on the displayed images including changing image characteristics (e.g., magnification, brightness, contrast, etc.), adding notes or text, locally storing images, etc.

Using the server 108 to initially route the report 500 and embed the link 502 allows a recipient, such as the ordering physician, to communicate with many different report sources 102 and image repositories 106 (e.g., different RISs, PACSs, etc.) without requiring dedicated infrastructure (e.g., HL7 interfaces, VPNs, etc.) between the parties. Using the server 108 also allows the location of stored images to change without breaking the embedded link 502. For example, if an image repository 106 (e.g., a PACS) is upgraded, the server 108 can be reconfigured to automatically access the upgraded repository 106 for requested images without needing to provide the recipient with a new link 502. Similarly, if a PACS becomes available in a cloud storage environment, the server 108 can be reconfigured to automatically access the cloud environment rather than the PACS even when a user clicks an embedded link 502 generated before images were available through the cloud storage environment. In particular, the server 108 uses the image directory to map requested images to an image repository 106 or associated image viewer 107. Accordingly, the image directory can be updated to allow the server 108 to provide access to stored images through the link 502 even as the stored images change storage locations or are accessible through different image viewers 107.

In some embodiments, the server 108 is configured to keep logs of routed reports (e.g., tracking successful deliveries, delivery failures, etc.). Therefore, the server 108 can provide a dashboard that allows users (e.g., imaging providers, referring physicians, server administrators, etc.) to track whether a particular report was successfully delivered and obtain various statistics regarding report status (e.g., sent, confirmed, failed, etc.) and usage of the server 108. For example, the server 108 can track what reports have been received from report sources 102 and what reports have been transmitted to the report destination 104. In some embodiments, the server 108 can also be configured to receive status notifications from the report destination 104 (e.g., through the network accessing the report destination, such as a clinical messaging network) regarding whether the report was successfully delivered to the report destination 104. In some embodiments, the report destination 104 can also provide information to the server 108 regarding what reports were accessed or viewed. The server 108 can provide this information or a portion thereof to users to allow users to track reports through the system 100. Also, in some embodiments, the server 108 can provide this information or a portion thereof to the report source 102, and the report source 102 can make this information available to users (see FIG. 3).

Figure 13:
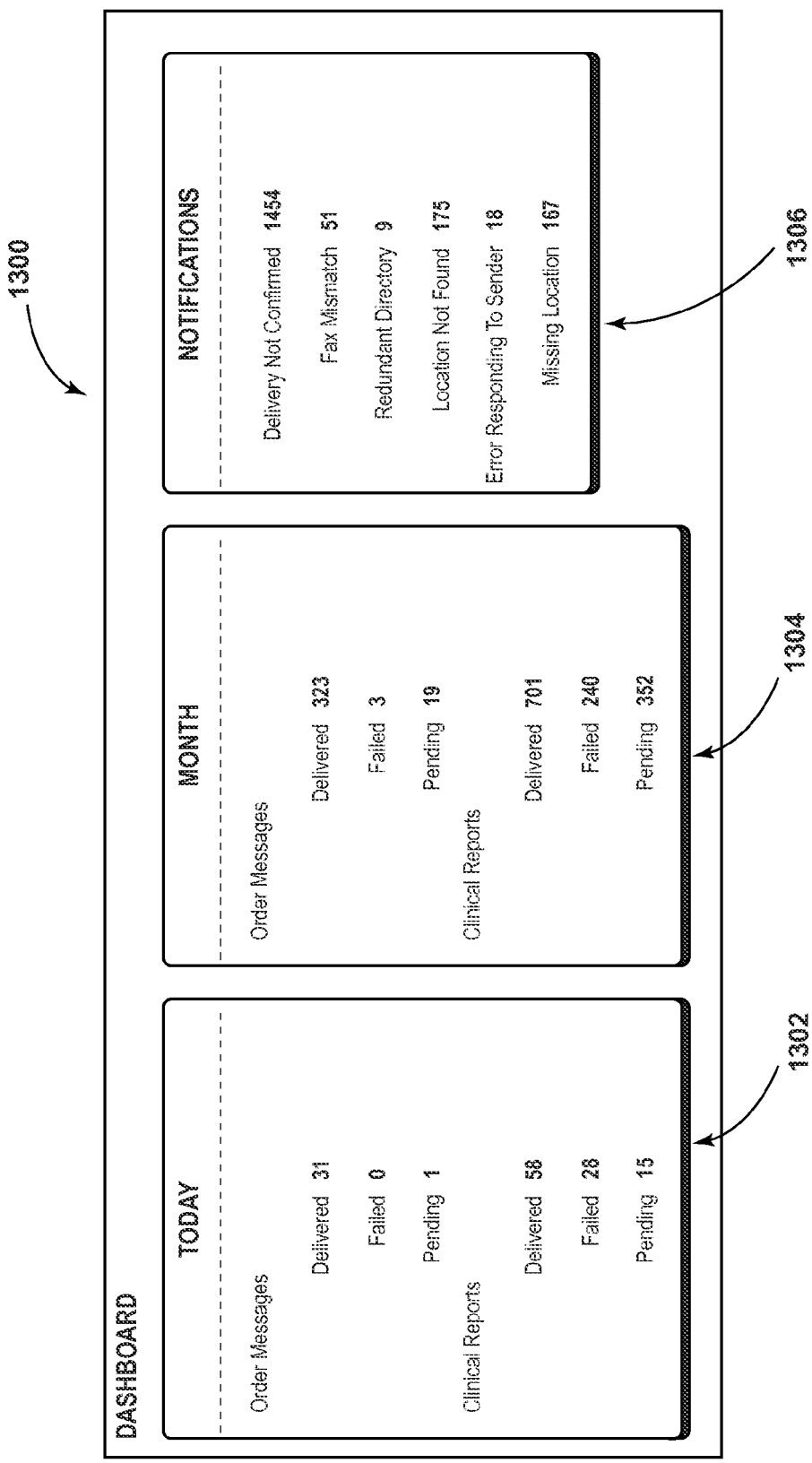
FIG. 13 is a screen shot illustrating a user interface, provided by the routing server included in the system of FIG. 1A, for providing statistics of reports handled by the routing server.

For example, FIG. 13 illustrates a user interface 1300 provided by the server 108 and remotely accessible over a network, such as web page accessible by a user over the Internet using a browser application. The interface 1300 includes current statistics 1302 (e.g., how many reports were delivered today) and historical statistics 1304 (e.g., how many reports were delivered for the current month). In some embodiments, the user interface 1300 also provides notification statistics 1306 regarding the number of notifications provided by the server 108, which can indicate failures, errors, and timeouts. It should be understood that the statistics provided in the user interface 1300 can be tied to authorizations or roles assigned to the user requesting the statistics. For example, a user associated with a single report source 102 may only be able to view statistics through the user interface 1300 regarding the associated report source 102. However, a user associated with multiple report sources 102 may be able to view statistics regarding multiple report sources 102 (e.g., individually or aggregated in one or more combinations).

In some embodiments, a user can also query the server 108 to track or obtain details regarding one or more reports. For example, FIG. 14 illustrates a user interface 1400 provided by the server 108 and remotely accessible over a network, such as a web page accessible by a user over the Internet using a browser application. The user interface 1400 allows a user to view details regarding one or more reports handled by the server 108. For example, as illustrated in FIG. 14, a user can use input mechanisms 1402 included in the interface 1400 to specify query parameters, such as a message identifier, an accession number, a date or date range, a status, recipient information, a report source, a report destination, an imaging provider, an imaging provider location, etc. The server 108 uses the query parameters to generate a list 1404 of matching reports, which the server 108 displays to the user. Accordingly, a user can use the interface 1400 to obtain details regarding a particular report, reports handled during a predetermined time period, reports sent to a particular recipient, etc.

Figure 15:
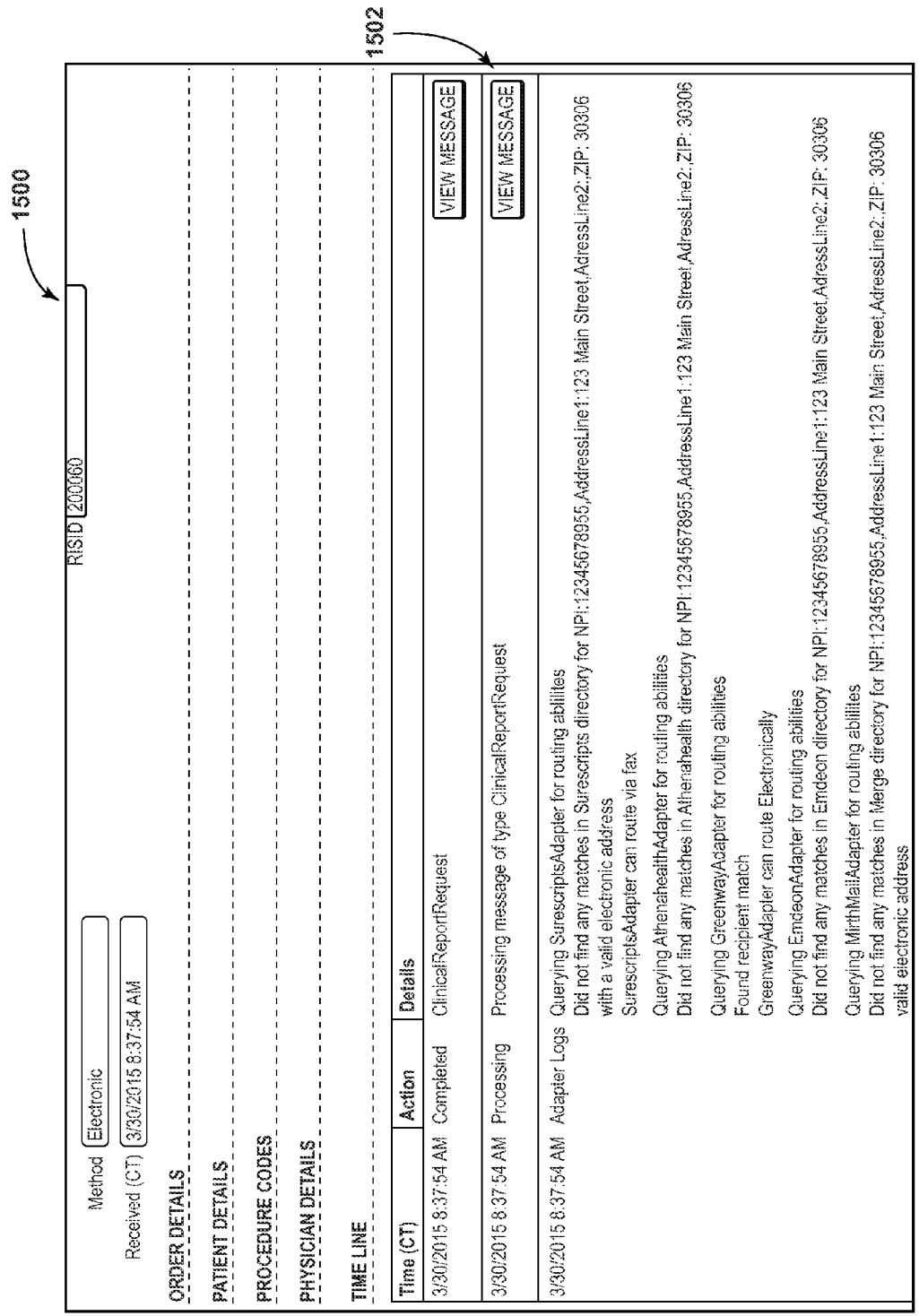
FIG. 15 is a screen shot illustrating a user interface, provided by the routing server included in the system of FIG. 1A, displaying a timeline report for the routing server.

Also, in some embodiments, the server 108 provides reporting functionality. For example, in some embodiments, the server 108 generates and provides reports to users. The reports can include default reports and customized reports. For example, as illustrated in FIG. 15, the server 108 can provide a user interface 1500 that displays a timeline report 1502. The timeline report 1502 sequentially identifies the interactions between one or more report sources 102 and the server 108 over a predetermined period (e.g., the past 24 hours, the past week, the past month, etc.). The server 108 can also provide a usage report. For example, FIG. 16 illustrates a user interface 1600 provided by the server 108 that allows a user to view a usage report 1602 providing usage statistics (e.g., number of reports sent, number of reports delivered, number of failures, etc.) for one or more report sources 102. In some embodiments, usage reports 1602 are used for billing purposes. In some embodiments, the server 108 also provides attestation reports, which can indicate a number of reports that were successfully delivered to the report destination, a number of reports that were accessed, and, optionally, a number of image sets assessed associated with delivered reports. Accordingly, the attestation reports can be used to provide information regarding a percentage of reports that are provided electronically and provide electronic access to the corresponding images. Again, the particular functionality, including the types of reports, available to a particular user can be based on the user's authorizations and/or assigned roles. Also, it should be understood that the reports generated by the server 108 can be provided through a user interface provided by the server 108 and remotely accessible over a network, such as a web page accessible by a user over the Internet using a browser application, or can be directly transmitted to users, such as attachments to an email message or as another electronic or non-electronic transmission (e.g., faxed, mailed, etc.).

Order Routing

In some embodiments, in addition to or as an alternative to the report routing described above, the server 108 can be used to route orders from a physician to the report source 102 (e.g., a RIS) or another system that handles procedure and patient scheduling (e.g., a HIS). Accordingly, a physician can place an order through the server 108 to ensure that a patient undergoes a recommended procedure and, optionally, uses an imaging provider associated with the physician (e.g., included in the same network).

Figure 17:
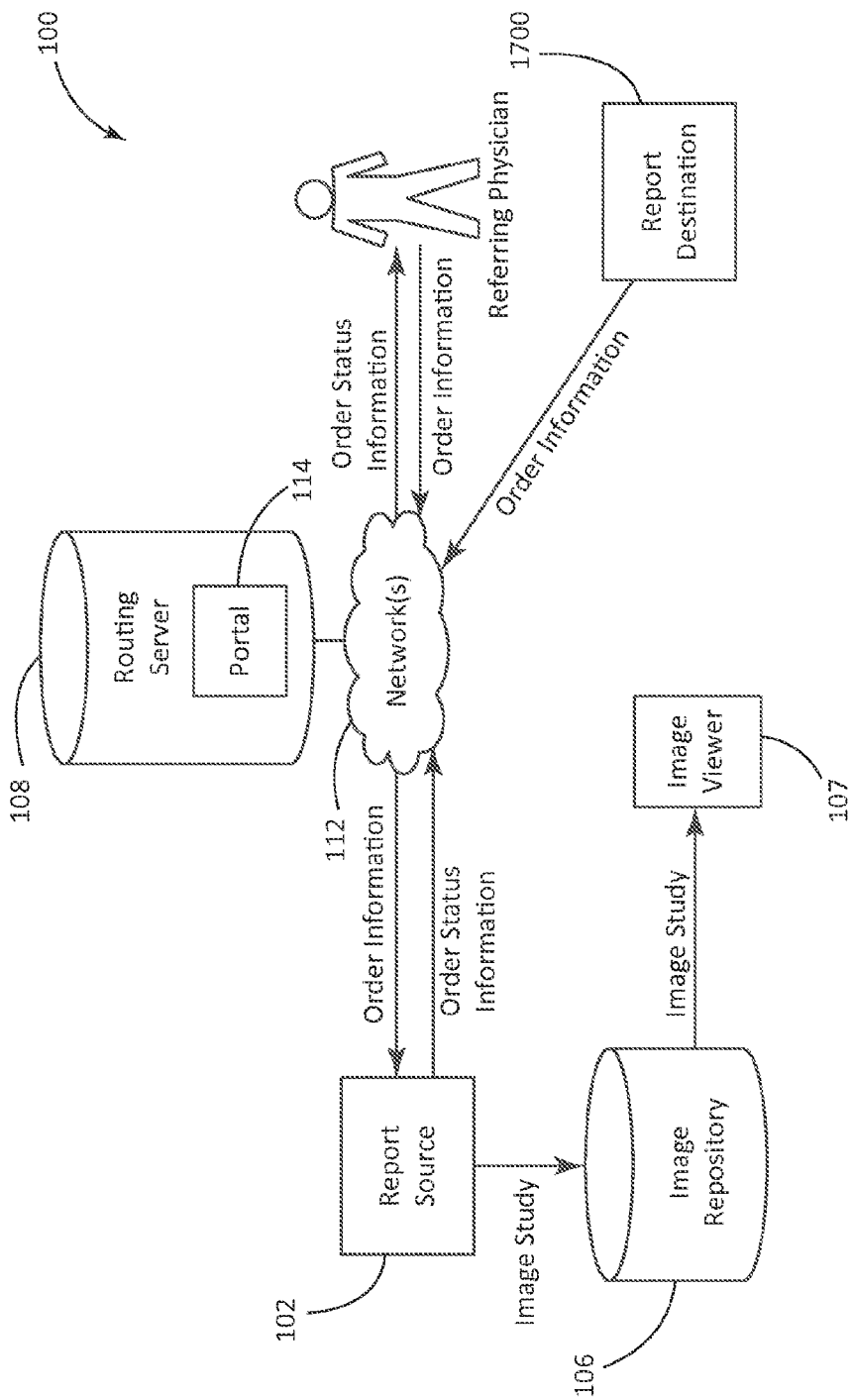
FIG. 17 schematically illustrates a system for routing orders for imaging procedures.

For example, as illustrated in FIG. 17, a referring physician can provide order information to the server 108. In some embodiments, the referring physician provides order information through a user interface provided by the server 108 that is remotely accessible over a network, such as web page accessible by a user over the Internet using a browser application. In addition or as an alternative, the referring physician can provide order information to the server 108 directly from an order source 1700, such as the referring physician's EMR system.

The server 108 routes received order information (or a portion thereof) to a report source 102 associated with an imaging provider (e.g., a RIS or a HIS). The imaging provider processes the order information to schedule the ordered procedure, perform the procedure to obtain an image study, and provide a completed image report based on the image study. Regardless of whether the resulting image report is distributed by the server 108 as described above, a referring physician can track the status of an order placed through the server 108 and, in some embodiments, can receive a completed report for an order and/or access the associated image study through the server 108. It should be understood that, as used in this section of the present application relating to order routing, a "referring physician" can include the referring physician (e.g., a patient's primary physician) or a user associated with the referring physician such as a nurse, an assistant, another physician in the same office as the referring physician, etc.

Figure 18:
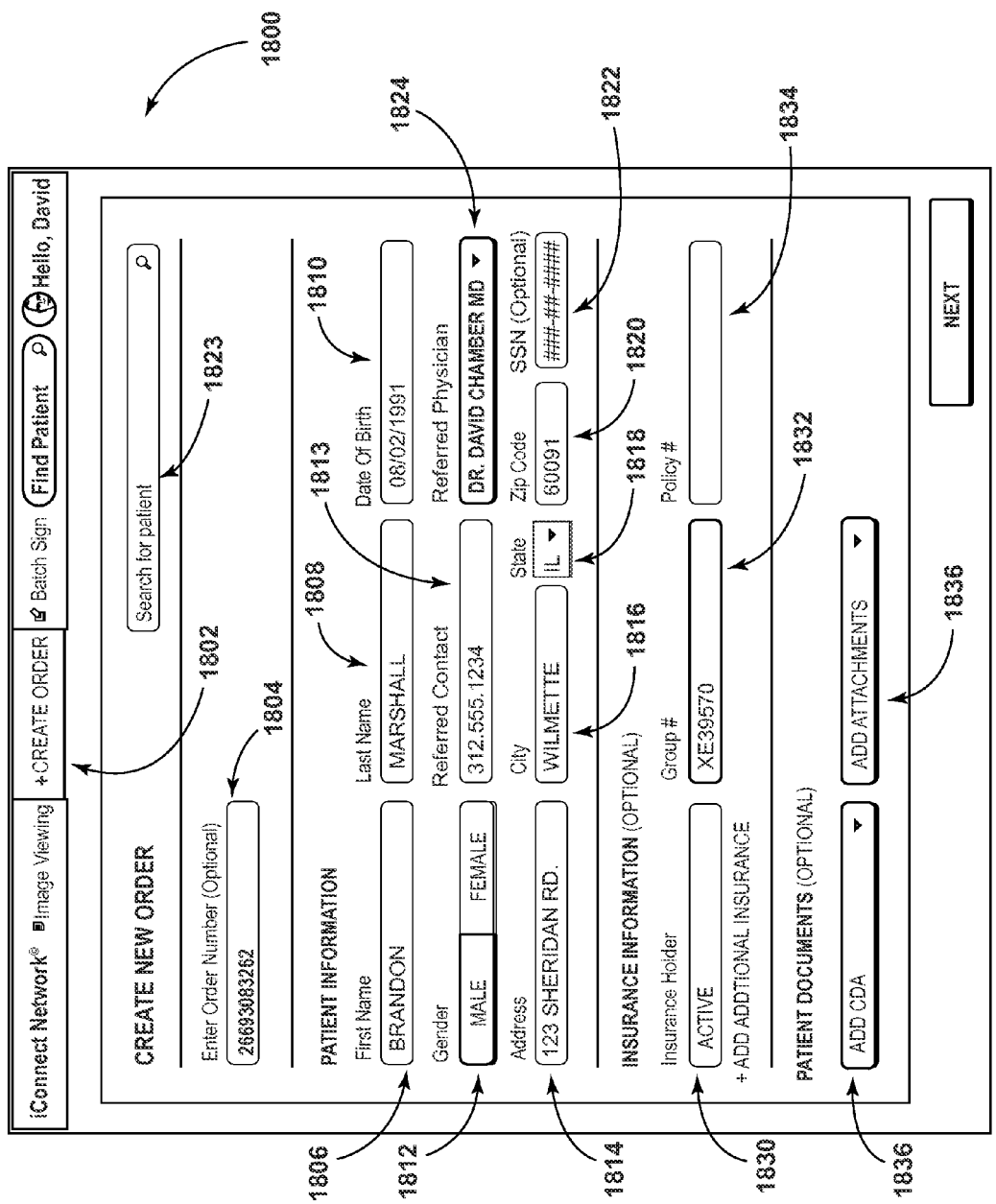

As noted above, to obtain order information from a referring physician, the server 108 can provide an interface remotely accessible over a network, such as a web page accessible by a user over the Internet through a browser application. For example, FIG. 18 illustrates a user interface 1800 that allows a referring physician to enter order information. In some embodiments, each imaging provider can be associated with their own version of the user interface 1800. Accordingly, a referring physician can receive a link (e.g., a URL) from each imaging provider that the referring physician works with (e.g., is within the referring physician's healthcare network or otherwise has an existing relationship with the referring physician). Creating a separate interface 1800 for each imaging provider allows an imaging provider to customize the interface 1800 and also limits the amount of information available to a referring physician (e.g., the referring physician only sees imaging locations associated with a particular imaging provider, which the referring physician has screened or otherwise is familiar with in terms of services and quality). However, in some embodiments, the server 108 can provide a central interface 1800 that a referring physician can access to place an order with one of multiple available imaging providers.

As illustrated in FIG. 18, a referring physician can create a new order using the interface 1800 by selecting a "Create Order" selection mechanism 1802. The interface 1800 then prompts the referring physician for order information. The order information can include an order number. For example, a referring physician can optionally specify an order number for a new order using an "Order Number" input field 1804. The order number can correspond to an order number managed by the referring physician's order source 1700. For example, in some embodiments, the referring physician places an order within the order source 1700, which automatically generates a unique number for the order. The referring physician can enter this unique number into the interface 1800 to correlate the order placed through the server 108 with the order placed through the order source 1700. For example, when a report is received in response to the order, the report can be linked with the order placed through the order source 1700. Also, in some embodiments, entering the order number from the order source 1700 into the interface 1800 can allow the server 108 to automatically pull order data from the order source 1700 (e.g., and automatically pre-populate one or more input fields and selection mechanisms provided through the user interface 1800). In other embodiments, the server 108 can be configured to assign a unique order number to each order.

The order information can include patient information. For example, as illustrated in FIG. 18, the referring physician can provide a patient's name using a "First Name" input field 1806 and a "Last Name" input field 1808, a patient's date of birth using a "Date of Birth" input field 1810, a patient's gender using a "Gender" selection mechanism 1812, and a patient's contact information using a "Preferred Contact" input field 1813, an "Address" input field 1814, a "City" input field 1816, a "State" selection mechanism 1818, and a "Zip Code" input field 1820. In some embodiments, the patient information also includes a patient's social security number ("SSN") or other unique identifier. For example, as illustrated in FIG. 18, the referring physician can use a "SSN" input field 1822 to provide a patient's SSN. In some embodiments, the user interface 1800 provides one or more search mechanisms 1823 that allow the referring physician to search for patient information rather than entering it manually (e.g., patient information previously entered through the interface 1800 and maintained by the server 108 and/or patient information managed by the order source 1700 and/or the report source 102). For example, if the referring physician entered patient information through the interface 1800 for a previous order, the referring physician may be able to use the search mechanisms 1823 to automatically populate patient information through the interface 1800.

The order information can also include referring physician information. For example, as illustrated in FIG. 18, the referring physician can provide a referring physician's name using a "Referring Physician" selection mechanism 1824. In some embodiments, the referring physician information also includes an office of the referring physician (e.g., to keep orders separate for different offices maintained by the referring physician).

In addition, the order information can include insurance information for the patient. For example, as illustrated in FIG. 18, a referring physician can provide the name of an insurance provider using a "Provider" input field 1830, an insurance group number using a "Group" input field 1832, and an insurance policy number using a "Policy" input field 1834. If a patient carries multiple insurance policies, the referring physician can enter insurance information for each policy.

Optionally, the referring physician can also attach one or more patient documents to the order (e.g., using one or more attachment selection mechanisms 1836). The attachments can include an electronic medical record, previous images, physician notes, or a continuity of care document (e.g., in the clinical document architecture ("CDA")).

Figure 19:
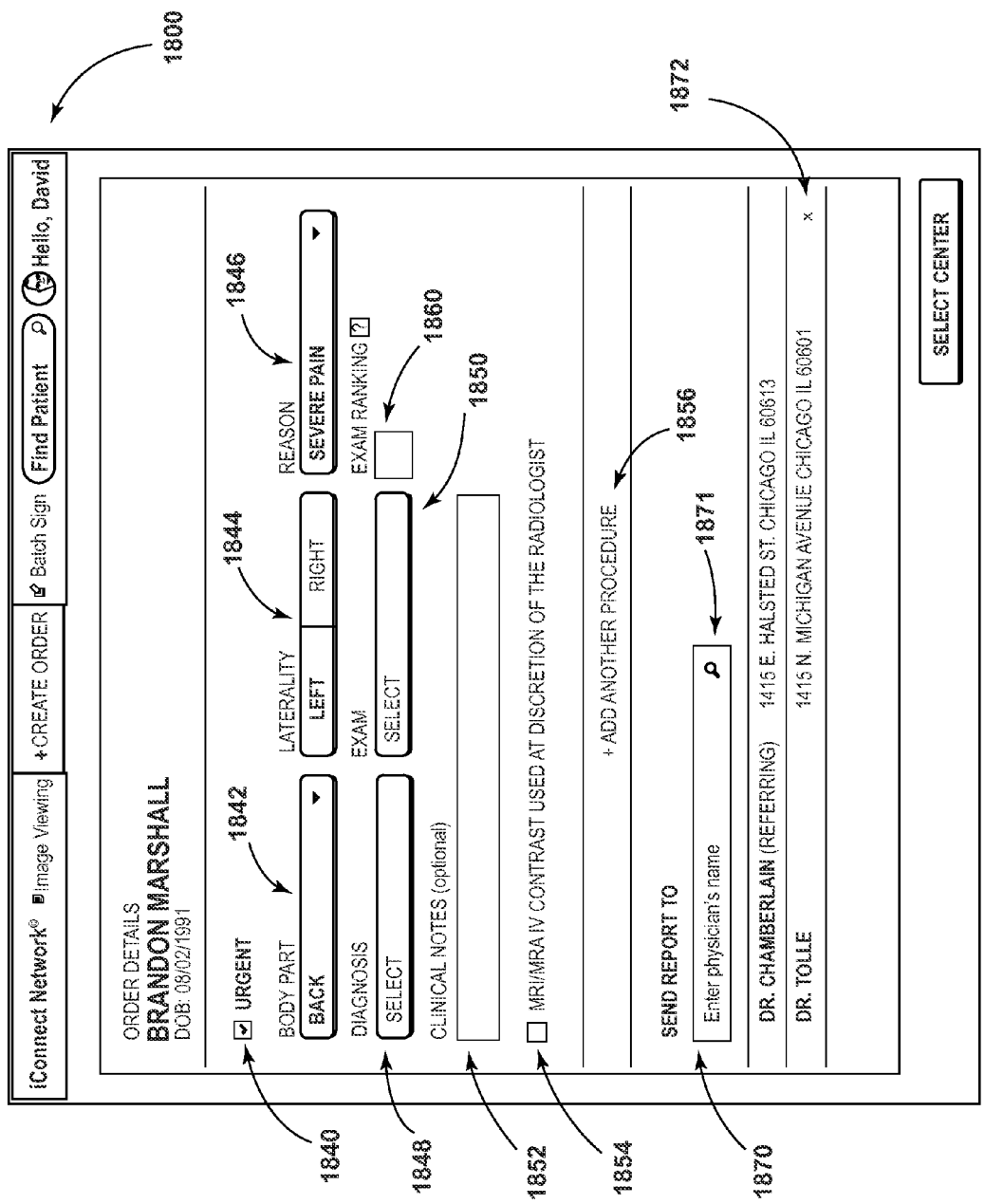

As illustrated in FIG. 19, the order information provided through the interface 1800 can include urgency information. For example, as illustrated in FIG. 19, the user interface 1800 also allows a referring physician to mark an order as urgent by selecting an "Urgent" selection mechanism 1840. In some embodiments, after a report is generated for an order, the imaging provider can also mark an order as urgent regardless of whether the referring physician initially marked the order as urgent (e.g., by transmitting an urgent identifier to the server 108 with a completed report).

The order information can also include image procedure information. For example, as illustrated in FIG. 19, the user interface 1800 can prompt the referring physician to select a body part being imaged using a "Body Part" selection mechanism 1842, a position of the body part being imaged using a "Laterality" selection mechanism 1844, a reason for the procedure using a "Reason" selection mechanism 1846, a diagnosis associated with the procedure using a "Diagnosis" selection mechanism 1848, and an exam selection using an "Exam" selection mechanism 1850. It should be understood that one or more of the selection mechanisms provided for specifying the imaging procedure being ordered can include one or more drop-down menu that allow the referring physician to select an input from a list. The lists can be correlated such that when the referring physician selects an input from one list, the other lists are customized. For example, if the referring physician selects "Back" as the body part for the imaging procedure, the user interface 1800 can be configured to automatically modify the list of selectable exams (e.g., provided through the "Exam" selection mechanism 1850). Accordingly, the user interface 1800 can aid the referring physician in selecting the right exam and other imaging procedure details.

As illustrated in FIG. 19, the referring physician can also provide notes associated with the imaging procedure (e.g., using a "Notes" input field 1852). In addition, the referring physician can indicate whether the imaging provider (e.g., the radiologist) can use a contrast agent for the imaging procedure at his or her discretion (e.g., using a "Discretion" selection mechanism 1854). Furthermore, as illustrated in FIG. 19, a user can add multiple procedures to an order (e.g., using an "Add Another Procedure" selection mechanism 1856).

Figure 20:
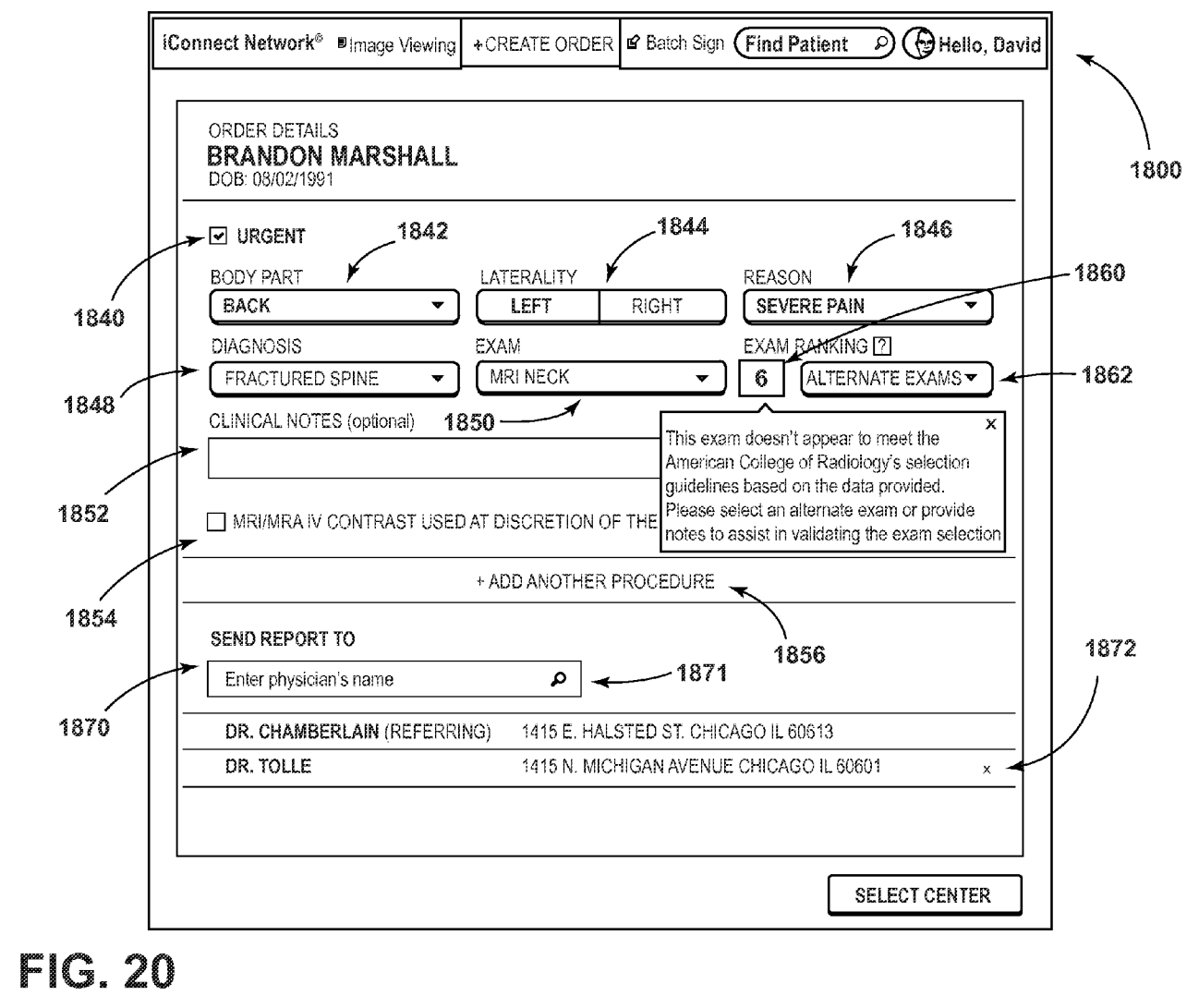
Figure 21:
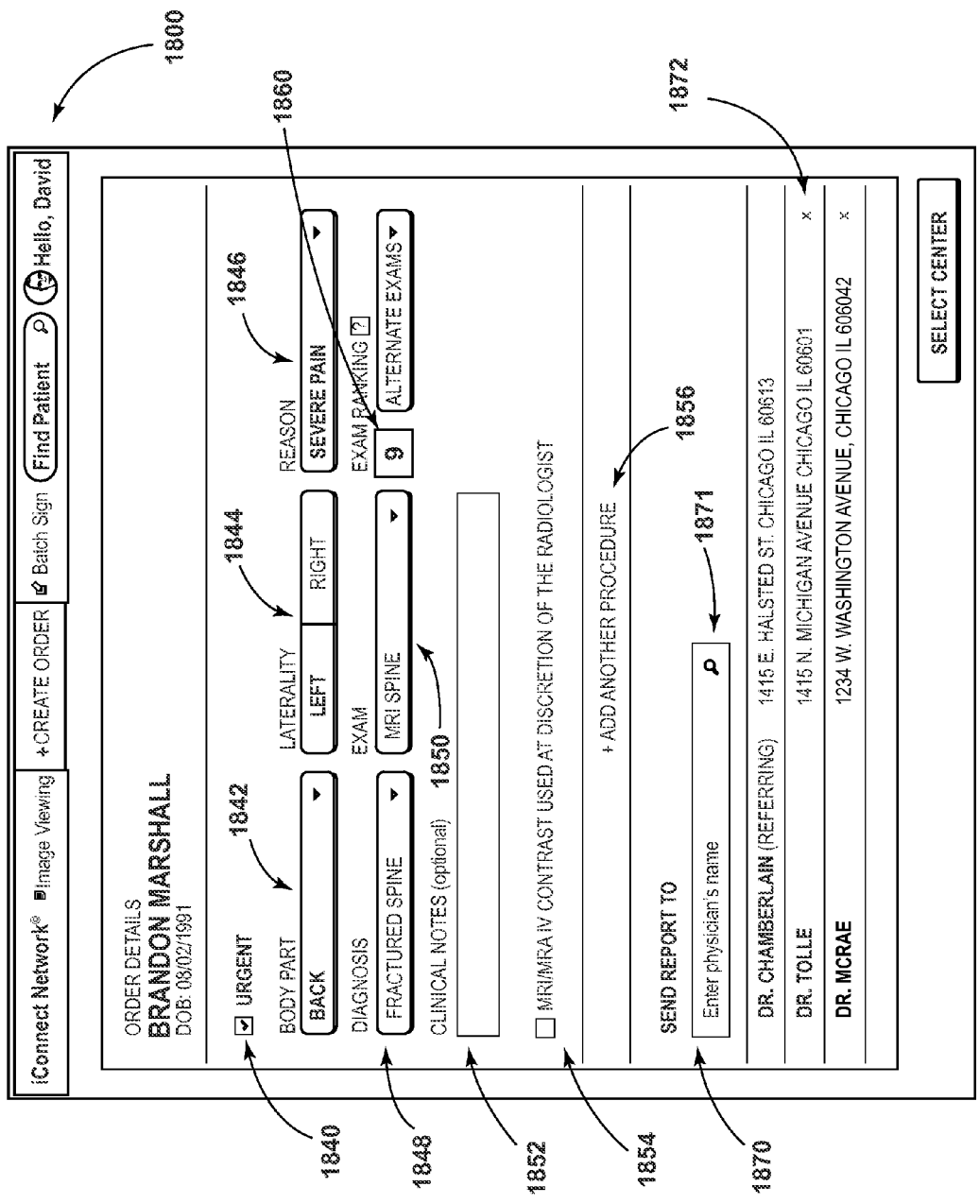

In some embodiments, the server 108 provides clinical decision support for a new order. For example, as illustrated in FIGS. 20 and 21, after a referring physician specifies an imaging procedure (e.g., an exam) for a new order, the server 108 compares the specified procedure to the associated patient information (e.g., the reason and/or body part specified for the procedure and urgency of the procedure) and other information to determine the appropriateness of the order (e.g., based on one or more rules, such as the American College of Radiology's selection guidelines). The server 108 then provides a ranking for the specified procedure based on appropriateness, which is displayed to the referring physician. For example, as illustrated in FIG. 20, the ranking can be displayed within an "Exam Ranking" section 1860. In some embodiments, as illustrated in FIGS. 20 and 21, the ranking can be color-coded. For example, in some embodiments, a ranking can be colored red to signify "Do Not Proceed," colored orange to signify "Proceed with Caution," and colored green to signify "Proceed." Accordingly, a physician can use the color-coding to understand whether he or she should revise the selected exam and/or other procedure information. Also, in some embodiments (see FIG. 20), a referring physician can select the displayed ranking (e.g., by hovering over the displayed ranking) to access an explanation regarding the ranking. In some embodiments, the ranking can also take into consideration any other procedures included in the new order or other orders.

Furthermore, in some embodiments, the server 108 can be configured to automatically suggest alternative exams (e.g., when the ranking is below a predetermined value or when other exams exist that have better rankings). For example, as illustrated in FIG. 20, the user interface 1800 can include an "Alternate Exams" selection mechanism 1862, which can include a drop-down of available exams. The drop-down of available exams can include those exams (e.g., applicable for the selected body part, laterality, reason, diagnosis, etc.) that have a higher ranking than the exam currently selected. For example, the server 108 can be configured to determine a ranking for each available exam provided through the "Exam" selection mechanism 1850 (which, as noted above, can be customized based on the user's selection of body part, laterality, reason, diagnosis, etc.). The server 108 then populates the drop-down list for the "Alternate Exams" selection mechanism 1862 with each exam having a higher ranking than the currently-selected exam. It should be understood that, in some embodiments, the server 108 provides the ranking only as a suggestion and does not prevent the referring physician from continuing the order process with the specified procedure.

In some embodiments, the order information also includes destination information that specifies one or more recipients for the image report ultimately generated for the order (e.g., the referring physician, other specialists, other physicians treating the same patient, etc.). For example, as illustrated in FIGS. 19-21, the user interface 1800 can include a "Send Report" input field mechanism 1870. A referring physician can manually enter destination information (e.g., a recipient name, email address, fax number, EMR system, etc.) using the "Send Report" input mechanism 1870. Alternatively or in addition, a referring physician can use a search selection mechanism 1871 to locate destination information (e.g., based on destination information entered by the referring physician in previous orders, destination information maintained by the server 108, destination information maintained by the report source 102 and/or the order source 1700, or a combination thereof). In some embodiments, the server 108 can also identify one or more default destinations, such as the referring physician. The user interface 1800 can display the default destination and any destinations selected by the referring physician within a list 1872, which the referring physician can modify (e.g., delete recipients) as desired.

Figure 22:
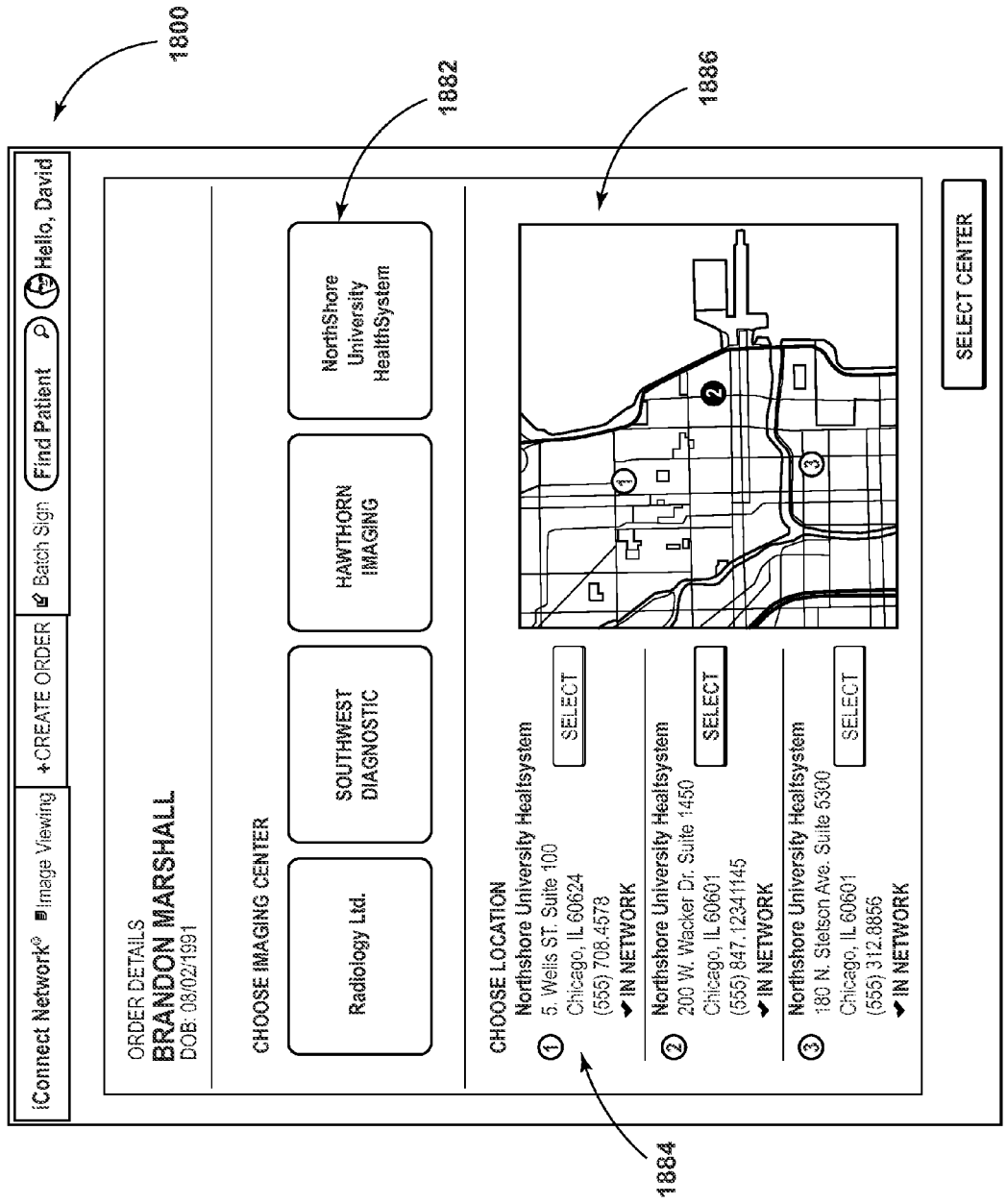

In some embodiments, the order information also includes imaging provider information. For example, as illustrated in FIG. 22, the user interface 1800 can prompt the referring physician to choose an imaging provider (sometimes referring to as an imaging center) from a list 1882 of available providers. As noted above, in some embodiments, the user interface 1800 can be associated with a specific imaging provider. Accordingly, in these situations, the referring physician does not need to select a specific imaging provider. The imaging provider information can also include imaging location information. For example, the user interface 1800 can include a list 1884 of locations associated with an imaging provider. The list 1884 can include address information and other information for each location (e.g., hours, accessibility options, insurance networks, etc.). In some embodiments, the user interface 1800 allows the referring physician to sort or filter locations included in the list 1884. For example, a referring physician can sort or filter the available locations by locations previously selected by the referring physician, by locations within a predetermined distance from the referring physician or another geographic location, by locations offering the imaging exam selected by the referring physician, by insurance networks, by availability, etc.

As illustrated in FIG. 22, in some embodiments, the user interface 1800 can also provide a map 1886 that graphically display a marker representing the geographical location of each location included in the list 1884 (and, optionally, a marker showing the referring physician's office location). To select a particular location, the referring physician can select a "Select" selection mechanism 1888 associated with the location.

In some embodiments, after entering order information, the server 108 requires that the order be signed by the referring physician. The server 108 can require that the order be signed by the actual physician placing the order. For example, if a referring physician's nurse or assistant enters the order information, the referring physician may be required to sign the order. As illustrated in FIG. 23, a referring physician can sign an order by entering credentials, such as a username and a password, using one or more "Credentials" input fields 1892 and selecting a "Sign Order" selection mechanism 1894. As illustrated in FIG. 23, the referring physician can provide notes for a signed order using a "Notes" input field 1896. Also, in some embodiments, the server 108 allows a referring physician to sign a batch of orders needing signature. For example, a user can select a "Batch Sign" selection mechanism 1898 provided through the use interface 1800 to view of list of orders needing signatures. The referring physician can then select one or more of the listed orders for signing with a single signature.

As illustrated in FIG. 17, once an order is signed, the order is routed by the server 108 to a report source 102 associated with the imaging provider (and location) specified in the order (e.g., a RIS or an HIS). In some embodiments, the report source 102 can be configured to store the received order as an order entered directly in the report source 102. Alternatively, the imaging provider receiving the order can use the received order to manually enter the order into the report source 102 (e.g., by printing a hard copy and manually entering the data from the printed copy into the report source 102).

Also, in some embodiments, the server 108 communicates with the report source 102 through a gateway. The gateway can be configured to poll the server 108 for new orders associated with the report source 102, and, when a new order is available on the server 108, the gateway receives the order information from the server 108, transforms the order information (e.g., to the health level 7 ("HL7") standard), and transfers the transformed order information to the report source 102. The gateway can be used to manage security requirements associated with the report sourced 102 or to simplify the interaction between the server 108 and a report source 102.

After receiving an order through any of the above mechanisms, the report source 102 processes the order. In particular, after the order has been entered into the report source 102 (e.g., automatically or manually), the order is scheduled. For example, the imaging provider can contact the patient to schedule the ordered procedure (e.g., automatically or by contacting the patient).

In addition, the report source 102 can process an order by verifying the order information and making changes to the order information as necessary. For example, an imaging provider may (e.g., manually or automatically) identify that a different procedure would be better for the order. These changes can be provided to the server 108, which can make the changes known to the referring physician. For example, the server 108 can generate one or more notifications (e.g., email messages, text messages, etc.) when changes are made to an order, which can be sent to the referring physician (and/or other recipients associated with the order). Alternatively or in addition, a referring physician can be notified of changes the next time he or she accesses the interface 1800 provided by the server 108. In some embodiments, when a referring physician access an order through the interface 1800 that has been changed, the interface 1800 marks the changes using highlighting or another mechanism. The referring physician can review the changes and can provide feedback (e.g., further changes). Also, in some embodiments, a referring physician can re-sign a change order to approve the changes. When an order is changed (e.g., by any user), the server 108 can be configured to save the changed order as a new version and preserve the previous version (e.g., for auditing purposes and to identify what changes have been made).

Figure 24:
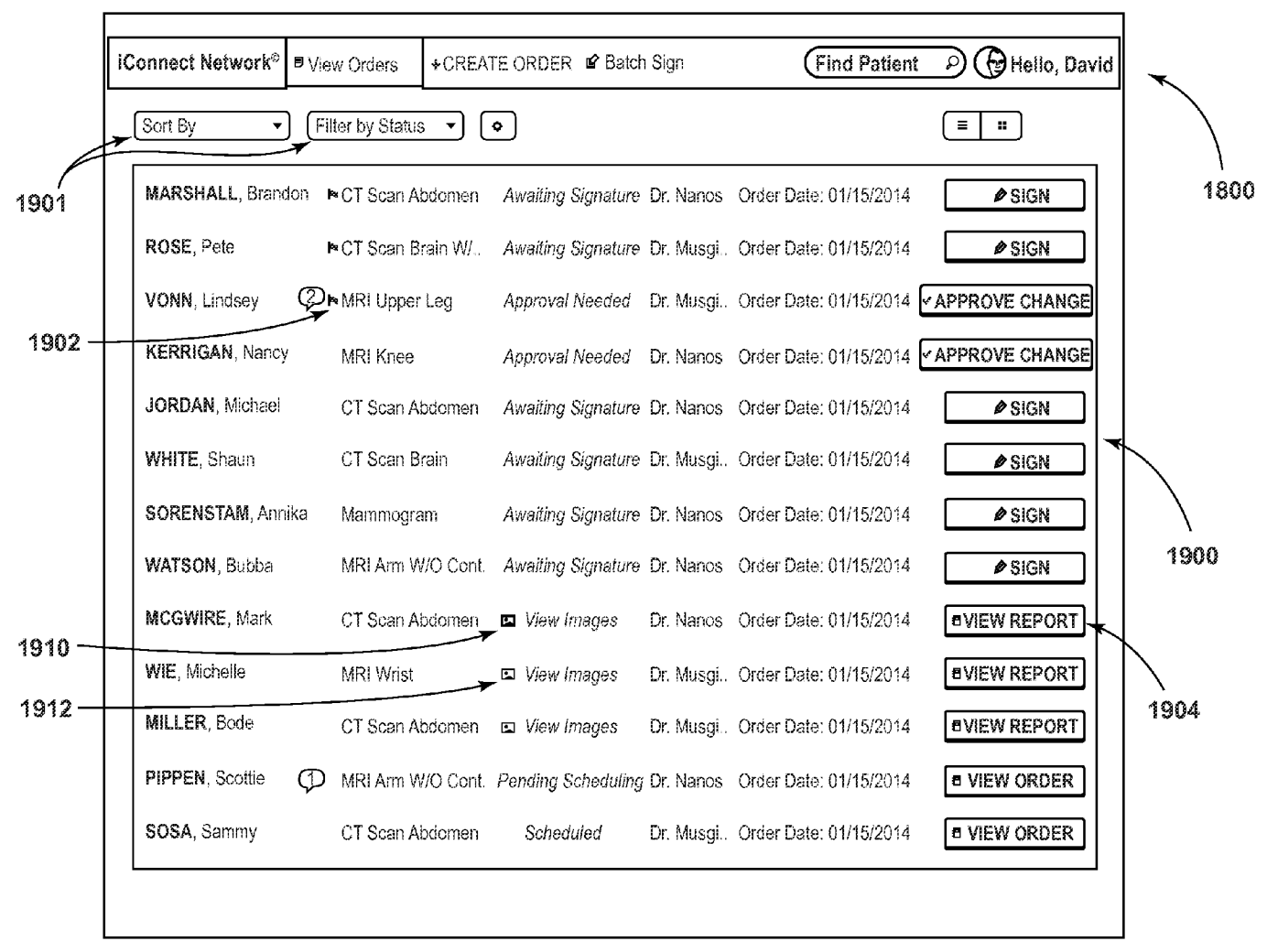

A referring physician can also use the interface 1800 to track the status of a submitted order. For example, as an order is processed, the report source 102 (or a gateway as described above) can transmit status information regarding the order to the server 108 (see FIG. 17). The server 108 makes the status information available to the referring physician through the interface 1800. For example, FIG. 24 illustrates the user interface 1800 displaying a list 1900 of orders placed through the server 108. A referring physician can use the list 1900 and one or more sorting/filtering selection mechanisms 1901 to identify what orders are in progress, what orders are complete (e.g., a report is available), what orders are awaiting signatures, what orders are urgent (e.g., designated with an icon 1902, such as red flag), what orders are awaiting change approvals, etc. For each listed order, the referring physician can select a "View Order" selection mechanism 1904 to view details associated with an order.

In some embodiments, a referring physician can also set persistent sorting or filtering for orders tracked through the server 108. For example, a referring physician can request that displayed orders be filtered by date, status, etc. and save this setting as persistent filtering. Thereafter, each time the referring physician accesses the interface 1800 provided by the server 108, the displayed orders can be sorted and filtered according to the saved persistent filtering. The referring physician, however, can modify the sorting and filtering as needed (e.g., without modifying the persistent filtering or by turning off the persistent filtering).

In some embodiments, the referring physician can configure access settings for the interface 1800. For example, the referring physician can specify what orders or parts of an order can be viewed and/or manipulated by the referring physician's assistants or other personnel (e.g., whether assistants can view reports generated for orders and/or the associated images). Access settings can also be configured to allow a referring physician to see orders placed by other referring physicians. For example, in some embodiments, the server 108 can allow orders placed by referring physicians in an office to be viewed and/or edited by any physician in the same office (e.g., for back-up purposes if a particular referring physician is unavailable). Other groups of physicians can similarly be configured within the server 108 to allow one physician to view and/or edit the orders of another physician.

In some embodiments, a referring physician can also use the interface 1800 provided by the server 108 to access reports for completed orders. For example, in some embodiments, the report source 102 transmits completed reports to the server 108 (e.g., in addition to locally storing the reports), and the server 108 forwards the reports as described above. Alternatively or in addition, the server 108 can store a copy of the reports for access by the referring physician through the interface 1800. For example, as illustrated in FIG. 24, the interface 1800 can provide a "View Report" selection mechanism 1910 and/or a "View Images" selection mechanism 1912 that a referring physician can select to view the report and/or images associated with an order. In some embodiments, the report stored by the server 108 can include the embedded link as described above. Also, as the interface 1800 provided by the server 108 can initially prompt a referring physician for credentials (as part of authorizing access to the interface 1800), the server 108 can use these credentials to automatically log the referring physician into an image viewer 107 for accessing images associated with a report provided through the interface 1800 (see FIG. 11).

It should be understood that the server 108 can provide statistics and reporting functionality as described above for report routing and for order routing. For example, the server 108 can be configured to provide statistics and reports regarding the number of orders transmitted, the number of notifications generated for any such orders, timeline reports, usage reports, etc.

Pre-Authorization

In some embodiments, in addition to or as an alternative to the report routing and/or the order routing described above, the server 108 is configured to manage a pre-authorization process for a submitted order. For example, in some embodiments, when a report source 102 (e.g., a RIS or an HIS) associated with an imaging provider receives an order (outside of the server 108), the report source 102 identifies (e.g., manually or by executing a set of predetermined rules) whether the order requires insurance pre-authorization. If pre-authorization is required, the report source 102 can inform the server 108 of the requirement and provide the server 108 with information regarding the order.

In other embodiments, if an order is submitted through the server 108 as described above, the report source 102 can receive the order, execute the rules, and notify the server 108 of the pre-authorization requirement similar to providing status updates for an order as described above. In these situations, the report source 102 may not provide the server 108 with information regarding the order (e.g., besides an identifier of the order, such as a unique order number and an indication that pre-authorization is required) since the server 108 already has the order information. For orders initially submitted through the server 108, the server 108 can use the pre-authorization information received from the report source 102 like any other status information for an order. For example, as illustrated in FIG. 25, the server 108 can be configured to set a status of an order requiring pre-authorization to "Awaiting Pre-Authorization" or "Pre-Authorization In Progress."

It should also be understood that in some embodiments, in addition or as an alternative to the report source 102 applying the pre-authorization rules, the server 108 can be configured to automatically apply pre-authorization rules to orders submitted to the server 108 to identify those orders requiring pre-authorization.

It should also be understood that in some embodiments, the server 108 is configured to manage pre-authorization processes for both orders submitted to the server 108 and orders submitted outside of the server 108. Accordingly, a user can use the server 108 to track pre-authorization processes for orders within a single user interface regardless of how an order was created.

Figure 26:
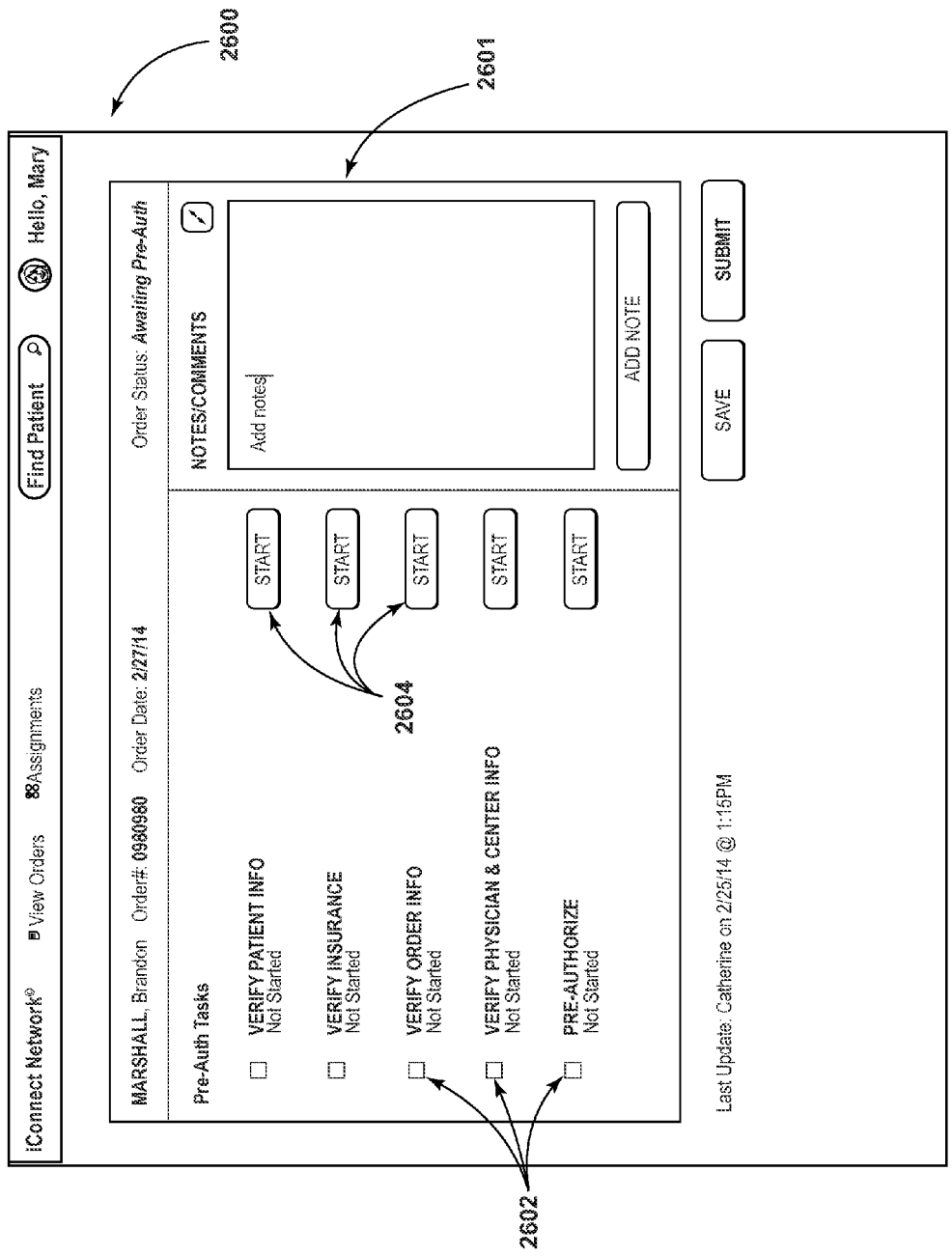
FIG. 26 is a screen shot illustrating a user interface for performing a pre-authorization process.

In addition to tracking the status or identifying orders requiring pre-authorization (and providing such information through the user interface 1800), the server 108 can manage the pre-authorization process. For example, the server 108 can provide an interface remotely accessible over a network, such as web page accessible by a user over the Internet through a browser application. The user interface can allow a user (i.e., a user authorized to perform pre-authorizations) to access orders requiring pre-authorization and perform pre-authorization tasks. For example, FIG. 26 illustrates a user interface 2600 provided by the server 108. The user interface 2600 provides a checklist or workflow for completing a pre-authorization process (e.g., verifying insurance, verifying patient information, verifying order information, verifying physician and imaging center information, and obtaining the pre-authorization). Accordingly, a user performing a pre-authorization process can use the server 108 to identify an order needing pre-authorization, obtain a checklist for completing a pre-authorization process for the order, and track progression through the checklist.

For example, as illustrated in FIG. 26, during the pre-authorization process, a user can enter notes using a "Notes" input field 2601. It should be understood that in some embodiments, notes entered by a user can be associated with a particular task of the pre-authorization process. However, the notes can be combined and displayed within a common field. It should also be understood that different access settings can be assigned to the notes and other input provided to the user interface 2600 during the pre-authorization process. For example, in some embodiments, only the user performing the pre-authorization process (and, optionally other users authorized to perform pre-authorizations) can view and/or edit the input. However, in other embodiments, individuals authorized to view the order undergoing the pre-authorization process, such as the referring physician and the imaging provider, can view the input. Accordingly, in these embodiments, the referring physician and the imaging provider can view the input to track the progress of the pre-authorization process being performed for an order.

As illustrated in FIG. 26, the interface 2600 lists a plurality of tasks for performing a pre-authorization process for a particular order. Each task is associated with an icon 2602 that identifies the status of the task (e.g., uncompleted or completed). Each icon 2602 can change (e.g., automatically or manually) as a task is completed. Each task is also associated with a "Start" selection mechanism 2604. A user can select the "Start" selection mechanism 2604 to view the details or steps of a particular task and provide associated input (e.g., view data, provide verifications of data, etc.).

Figure 27:
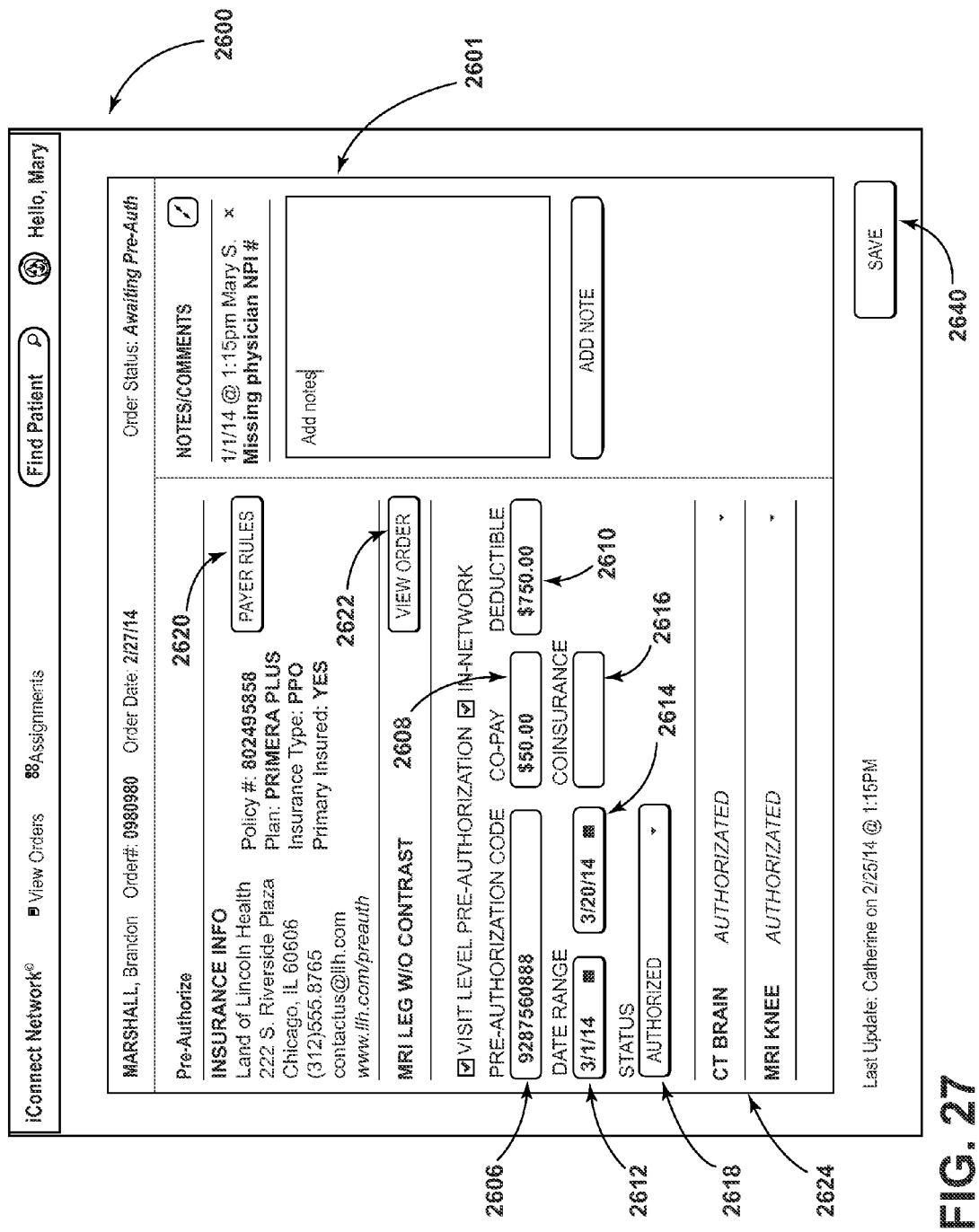
FIG. 27 is a screen shot illustrating a user interface for obtaining a pre-authorization code as part of a pre-authorization process.

For example, FIG. 27 illustrates the user interface 2600 displaying steps of a pre-authorization task and the information needed to complete the steps. For example, as illustrated in FIG. 27, the interface 2600 provides insurance information and at least a portion of the order information to allow a user to contact the patient's insurance company to obtain a pre-authorization code, which the user enters in a "Pre-authorization Code" input field 2606. The user interface 2600 can also allow a user to enter other information associated with the pre-authorization code, such as a co-pay amount using a "Co-Pay" input field 2608, a deductible amount using a "Deductible" input field 2610, a date range during which the authorization is valid using a start date selection mechanism 2612 and an end date selection mechanism 2614, coinsurance information using a "Coinsurance" input field 2616, and a status (e.g., "Authorized") using a "Status" selection mechanism 2618.

As illustrated in FIG. 27, the user interface 2600 can also provide other information to aid the user in obtaining the authorization code and related information. For example, the user interface 2600 can include a "Payor Rules" selection mechanism 2620 that a user can select to access rules associated with the patient's insurance coverage. Similarly, the user interface 2600 can include a "View Order" selection mechanism 2622 that a user can select to access additional details regarding the order. Also, in some embodiments, the user interface 2600 includes a list 2624 of past procedures. The interface 2600 can also be configured to compare a current order to previous orders for the same patient to automatically identify when a new order is for a procedure that was previously performed for the patient. If the newly-ordered procedure is a repeat procedure, the user interface 2600 can alert the user.

After a user enters the pre-authorization code and related information into the user interface 2600, the user can select a "Save" or "Submit" selection mechanism 2640 to save the entered details. Also, after the pre-authorization details are entered, the server 108 can automatically notify the report source 102 associated with the order that the pre-authorization process is complete and can, optionally, provide the report source 102 with the pre-authorization code and/or related information (e.g., directly or through a gateway as described above). In this situation, the report source 102 can process the order as described above (e.g., contact the patient to schedule the procedure, automatically schedule the procedure, etc.). In some embodiments, however, the report source 102 can process an order even if a pre-authorization process for the order has not been completed.

When a task included in the pre-authorization process is completed, the user interface 2600 can also automatically update the icon 2602 associated with the task (see FIG. 26). In other embodiments, a user can manually change an icon 2602 (e.g., by selecting or clicking on the icon 2602). Also, in some embodiments, the server 108 automatically updates the status of the order after the pre-authorization process is complete (e.g., as illustrated in FIG. 25). It should be understood that one or more of the tasks or one or more of the steps associated with a task can be automatically performed (e.g., by the server 108 or through a third-party system or service).

Figure 28:
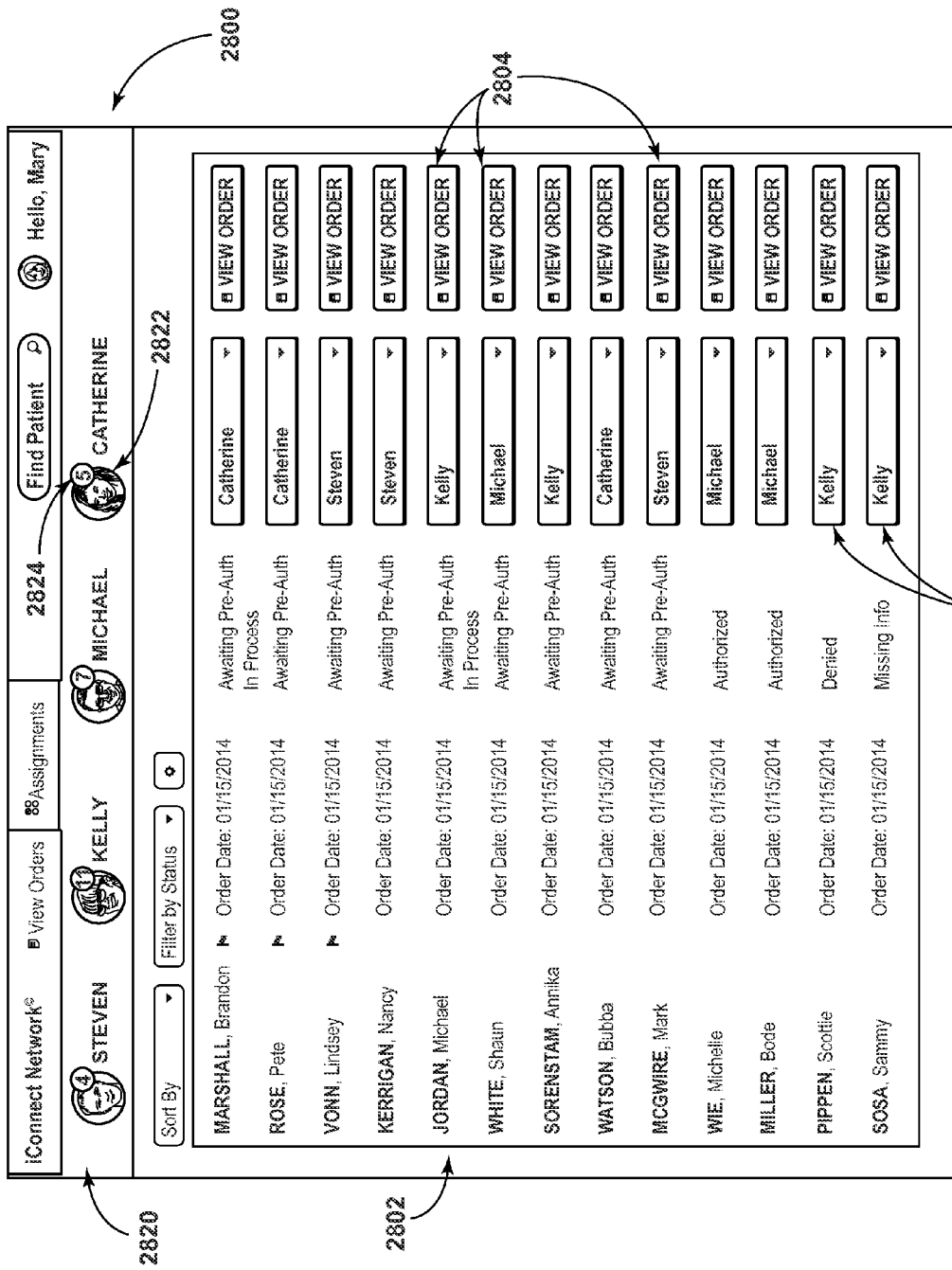
FIG. 28 is a screen shot illustrating a user interface for assigning an order requiring pre-authorizations to a user.

Furthermore, in some embodiments, the server 108 provides functionality for managing a team of users performing pre-authorizations. For example, as illustrated in FIG. 28, the server 108 can provide a user interface 2800 remotely accessible over a network, such as web page accessible by a user over the Internet through a browser application. The user interface 2800 allows a user (e.g., a manager of a team of users performing pre-authorizations) to view a list 2802 of orders needing pre-authorizations. Each order included in the list 2802 can be associated with a "View Order" selection mechanism 2804 that allows the user to access details regarding the order. Each order included in the list 2802 is also associated with an assignment selection mechanism 2806. Each assignment selection mechanism 2806 can include a menu (e.g., a drop-down menu) of available team members for performing pre-authorizations. Accordingly, the team manager can use the assignment selection mechanism 2806 to assign a particular order to a particular team member. After an order is assigned to a team member, the team member can be notified of the order. For example, in some embodiments, when a team member logs into the user interface 2800, the interface 2800 notifies the member of his or her assigned orders. Alternatively or in addition, the server 108 can generate a notification (e.g., an email message, text message, voice message, etc.) that alerts the team member of the assigned order. In some embodiments, the menu of available team members can be automatically customized based on details of the associated order. For example, if an order is associated with a particular insurance company, the menu of available team members may be filtered to only include those teams members familiar with the insurance company. Similarly, the menu of available team members may be filtered based on the backlog of each team member (e.g., to aid equal distribution of assignments). Also, in some embodiments, team members can use the assignment selection mechanism 2806 to personally select orders to process (as compared to being assigned an order by the team member).

As also illustrated in FIG. 28, the user interface 2800 can provide a dashboard 2820. The dashboard 2820 provides information regarding one or more of the team members performing pre-authorizations. For example, as illustrated in FIG. 28, the dashboard 2820 can include a graphical representation 2822 of a team member and an indication 2824 of the number of orders assigned to the team member. Accordingly, a team manager and team members can use the dashboard to quickly and efficiently identify the work load of each member. In some embodiments, the user interface 2800 also allows an order to be re-assigned to a different team member (e.g., for workload balancing). This functionality, however, may only be provided to team managers.

It should be understood that the server 108 can provide statistics and reporting functionality as described above for report routing for pre-authorization management. For example, the server 108 can be configured to provide statistics and reports regarding the number of pre-authorization requests received, the number of pre-authorization processes completed, the time required to complete one or more pre-authorization processes, the number of notifications generated for any pre-authorization processes, timeline reports, usage reports, etc.

It should be understood that the server 108 can be configured to provide report routing, order routing, pre-authorization, or any combination thereof. Also, in some embodiments, when the server 108 is configured to perform both report routing and order routing, a generated report can be delivered as described above for report routing and be made available with a user interface provided by the server 108 as described above for order routing. Also, it should be understood that functionality described in the present application as being performed by the server 108 can be distributed among multiple servers. Furthermore, the functionality described here as being performed by the server 108 can be performed by the user interfaces provided by the server 108 and vice versa.

Thus, embodiments of the invention provide methods and systems for managing image orders, reports, and/or pre-authorizations using network connections, such as the Internet. Accordingly, the methods and systems described herein eliminate the need for entities to establish and maintain direct connections within a dynamic and evolving industry.

Various features and advantages of the invention are set forth in the following claims.

What is claimed is:

1. A method of managing access to a set of images generated as part of a medical imaging procedure, the set of images stored in a first image repository accessible through a first image viewer, the set of images assigned a first identifier, the method comprising:
  receiving, with a server, a report from a first computer system, the report including an analysis of the set of images and excluding the set of images;
  storing, with the server, the first identifier of the set of images and a second identifier of the first image viewer in an image directory, wherein the first identifier is mapped to the second identifier within the image directory;
  automatically, with the server, creating a link for the set of images, the link including the first identifier of the set of images;
  identifying, with the server, a second computer system configured to receive the report and make the report accessible to a user;
  transmitting, with the server, the report and the link to the second computer system;
  when the user selects the link, automatically, with the server, identifying, using the first identifier of the set of images included in the link, the second identifier of the first image viewer mapped to the first identifier within the image directory;
  automatically, with the server, providing the user with access to the first image viewer to allow the user to view at least one image included in the set of images;
  updating, with the server, the image directory to map the first identifier to a third identifier of a second image viewer providing access to the set of images as stored in a second image repository;
  when the user selects the link after updating the image directory, automatically, with the server, identifying, using the first identifier of the set of images included in the link, the third identifier of the second image viewer mapped to the first identifier within the image directory; and
  automatically, with the server, providing the user with access to the second image viewer to allow the user to view at least one image included in the set of images.

2. The method of claim 1, wherein the first identifier of the set of images includes an accession number assigned to the set of images by a radiology information system.

3. The method of claim 1, further comprising embedding, with the server, the link into the report and wherein transmitting the report and the link to the second computer system includes transmitting the report with the embedded link to the second computer system.

4. The method of claim 1, wherein identifying the second computer system configured to receive the report includes identifying the user, accessing a recipient directory, and identifying the second computer system associated with the user within the recipient directory.

5. The method of claim 4, further comprising matching, with the server, the report to order information for the medical imaging procedure and wherein identifying the user includes identifying the user from the order information.

6. The method of claim 1, wherein identifying the second computer system configured to receive the report includes identifying a clinical messaging network communicating with the second computer system using direct messaging.

7. The method of claim 1, wherein transmitting the report and the link to the second computer system includes transmitting the report and the link to an electronic medical record system accessible by the user.

8. The method of claim 1, wherein automatically providing the user with access to the first image viewer includes providing the user with a second link for remotely accessing the first image viewer through a network connection.

9. The method of claim 1, wherein automatically providing the user with access to the first image viewer includes redirecting the user to the first image viewer.

10. The method of claim 1, wherein automatically providing the user with access to the first image viewer includes obtaining, with the server, credentials for the user for the first image viewer and submitting the credentials to the first image viewer with the server.

11. The method of claim 10, wherein obtaining the credentials for the user for the first image viewer includes prompting the user for the credentials.

12. The method of claim 10, wherein obtaining the credentials for the user for the first image viewer includes obtaining stored credentials.

13. The method of claim 1, further comprising sending, with the server, a notification to the first computer system after transmitting the report and the link to the second computer system.

14. The method of claim 1, further comprising receiving, with the server, a notification when the report and the link are received at the second computer system.

15. The method of claim 1, further comprising receiving, with the server, a notification when the report is accessed by the user via the second computer system.

16. The method of claim 1, further comprising providing, with the server, a user interface remotely accessible through a network connection, the user interface displaying details of reports received with the server and reports and links transmitted with the server over a period of time.

17. A system for managing access to a set of images generated as part of a medical imaging procedures, the set of images stored in a first image repository accessible through a first image viewer, the set of images assigned a first identifier, the system comprising:
a server configured to communicate with a first computer system over at least one network connection, the server configured to
receive a report from the report source, the report including an analysis of the set of images and excluding the set of images,
store the first identifier of the set of images and a second identifier of the first image viewer in an image directory,
automatically create a link for the set of images, the link including the first identifier of the set of images,
identify a second computer system configured to receive the report and make the report accessible to a user,
transmit the report and the link to the second computer system,
when the user selects the link, automatically identify, using the first identifier of the set of images included in the link, the second identifier of the first image viewer mapped to the first identifier within the image directory,
automatically provide the user with access to the first image viewer to allow the user to view at least one image included in the set of images,
update the image directory to map the first identifier to a third identifier of a second image viewer providing access to the set of images as stored in a second image repository,
when the user selects the link after updating the image directory, automatically identify, using the first identifier of the set of images included in the link, the third identifier of the second image viewer mapped to the first identifier within the image directory, and
automatically provide the user with access to the second image viewer to allow the user to view at least one image included in the set of images.

18. The system of claim 17, wherein the server is configured to identify the second computer system by identifying the user for the report, accessing a recipient directory, and identifying the second computer system mapped to the user within the recipient directory.

19. The system of claim 17, wherein the server further includes a portal providing access to user interfaces accessible over the at least one network connection and wherein the server is configured to automatically provide the user with access to the first image viewer by prompting, through a user interface provided by the portal, the user for credentials for the first image viewer and submitting the credentials to the first image viewer.

20. Non-transitory computer-readable medium comprising instructions that, when executed by an electronic processor, perform a set of functions, the set of functions comprising:
receiving a report from a first computer system, the report including an analysis of a set of images generated as part of a medical image procedure, the report excluding the set of images;
storing, in an image directory, a first identifier of the set of images and a second identifier of a first image viewer providing access to the set of images, wherein the first identifier is mapped to the second identifier within the image directory;
automatically creating a link for the set of images, the link including the first identifier of the set of images;
identifying a second computer system configured to receive the report and make the report accessible to a user;
transmitting, to the second computer system, the report and the link;
when the user selects the link, automatically identifying, using the first identifier of the set of images included in the link, the second identifier of the first image viewer mapped to the first identifier within the image directory;
automatically providing the user with access to the first image viewer to allow the user to view at least one image included in the set of images;
updating the image directory to map the first identifier to a third identifier of a second image viewer providing access to the set of images as stored in a second image repository without updating the link;
in response to the user selecting the link after updating the image directory, automatically identifying, using the first identifier of the set of images included in the link, the third identifier of the second image viewer mapped to the first identifier within the image directory; and
automatically providing the user with access to the second image viewer to allow the user to view at least one image included in the set of images.

* * * * *